United States Patent [19]

Priest et al.

[11] 3,954,749

[45] May 4, 1976

[54] BETA-AMINO CARBONYL CATALYSTS FOR POLYURETHANE PREPARATION

[75] Inventors: David Charles Priest, Charlotte, N.C.; Michael Ray Sandner, Charleston; David John Trecker, South Charleston, both of W. Va.

[73] Assignee: Union Carbide Corporation, New York, N.Y.

[22] Filed: Apr. 23, 1974

[21] Appl. No.: 463,247

Related U.S. Application Data

[62] Division of Ser. No. 309,906, Nov. 27, 1972, Pat. No. 3,821,131.

[52] U.S. Cl.......................................... 260/247.2 A
[51] Int. Cl.². ...................................... C07D 295/00
[58] Field of Search ............................ 260/247.2 A

[56] References Cited
OTHER PUBLICATIONS

Krakler, S. E., Chem. Abst., Vol. 58, 9299f, 1962.
Coble, G. W., Chem. Abst., Vol. 57, 16898c, 1962.

Primary Examiner—Lorraine A. Weinberger
Assistant Examiner—P. J. Killos
Attorney, Agent, or Firm—Marylin Klosty

[57] ABSTRACT

Provided as catalysts for the formation of cellular urethane polymers ranging from flexible to rigid foams, are beta-amino carbonyl compounds wherein carbonyl is present as an amido or carboxylic acid ester group and the beta-amino group is present as dialkylamino or an N-morpholino or N,N'-piperazino heterocyclic nucleus. Effective in the catalysis of the water-isocyanate reaction, these beta-amino amides and beta-amino esters are used with particular advantage in the manufacture of water-blown flexible foams, both molded and free-rise, including high-resilience and flame-retarded foam. The beta-amino carbonyl catalysts allow for the formation of foam products essentially free of the odor associated with amines such as N-ethylmorpholine. In view of this highly desirable characteristic and their other beneficial properties, the catalysts of the invention are advantageously employed as direct replacements for N-ethylmorpholine in high-resilience and other foam formulations.

3 Claims, No Drawings

BETA-AMINO CARBONYL CATALYSTS FOR POLYURETHANE PREPARATION

This is a division of application Ser. No. 309,906 filed Nov. 27, 1972, now U.S. Pat. No. 3,821,131.

BACKGROUND OF THE INVENTION

This invention pertains to particular betamino carbonyl compounds as catalysts for the formation of urethane polymers by the reaction of organic isocyanates with active hydrogen-containing compounds.

It is well known to the art that urethane polymers are provided by the reaction of organic polyisocynates and active hydrogen-containing organic compounds, usually in the presence of one or more activators, and that blowing action is provided when cellular products including flexible, semi-flexible, and rigid foams, are desired. It is also known that a number of different chemical reactions occur during polymer formation and expansion. For example, in addition to the chainextending, urethane-forming reaction between free isocyanate groups and active hydrogen, initially formed urethane linkages bearing secondary hydrogen may also function as a source of active hydrogen and react with additional isocyanate to form cross-links between polymer chains. Further, in water-containing systems such as those employed for the manufacture of flexible foams, isocyanate is also consumed by reaction with water, thereby generating carbon dioxide blowing agent in situ, and introducing further cross-links comprising urea groups. The nature of the cellular structure and the physical and mechanical properties of the foam are influenced by the extent of such reactions, and the relative rates and point in time at which they occur. Although balancing these variables so as to achieve a particular type or grade of foam can be controlled to some extent by the functionality, molecular weight and other structural features of the polyisocyanate and active hydrogen-containing reactants, the catalyst system also plays a significant role in this respect.

Among the relatively few compounds that have achieved widespread commercial application as catalysts in poluurethane manufacture are: tertiary amines consisting of carbon, hydrogen and nitrogen, as typically illustrated by 1,4-diazabicyclo[2.2.2]octane ("triethylenediamine") and N,N,N',N'-tetramethyl-1,3-butanediamine; and tertiary amines consisting of carbon, hydrogen, nitrogen and oxygen wherein oxygen is present as ether oxygen, as typically illustrated by bis[2-(N,N- dimethylamino)ethyl]ether and N-ethylmorpholine. With particular reference to the manufacture of flexible polyether polyol-based urethane foams, such tertiary amines are usually employed in combination with auxiliary catalysts comprising organic derivatives of tin such as stannous octoate and dibutyltin dilaurate, in order to provide a synergistic activation of the chain-extending reaction.

A relatively recent advance in the area of flexible polyurethane foam technology which has triggered intensive research effort to develop improved activators, is the advent of reaction mixtures having a sufficiently high reactivity to provide more complete reactions during polymer formation and expansion, thereby eliminating the need in commercial practice to post-cure the foam at high temperatures (300°–500°F.) to obtain a product of satisfactory overall properties. In addition to the saving in cost which elimination of high temperature post-curing offers to the foam manufacturer, such highly reactive formulations also provide flexible foams of generally improved flammability characteristics, more linear and thus improved load/deflection properties, low flex fatigue, and greater resiliency. In view of this latter characteristic, such products are referred to generally as high-resilience foams. In view of the aforesaid combination of properties, high-resilience foam is particularly suited as cushioning material in automotive interiors. In the production of at least a substantial proportion of high-resilience foam being manufactured at the present time, the aforementioned N-ethylmorpholine is used as a major component of mixed catalyst systems. However, the usefulness of N-ethylmorpholine in the manufacture of high-resilience foam as well as other types of cellular urethanes, is attended with certain disadvantages. Thus, N-ethylmorphine suffers the very serious drawback of having a particularly strong amine odor. The large quantities of N-ethylmorpholine which are employed relative to other catalyst components of the foam formulation, causes an obnoxious atmosphere at and surrounding the foam manufacturing plant site and also provides foams having a strong residual amine odor. This compound is also associated with a number of serious toxic effects; see, for example, Plastics Technology, "Catalysts Improve As Their Need Increases" pages 47–49 (July 1972). Consequently, it is desirable and is a primary objective of this invention to find a direct replacement for N-ethylmorpholine in the production of high-resilience foam in particular and cellular urethane manufacture generally and thereby allow for at least a substantial reduction in the relatively large amounts presently employed. Various other objects and advantages of the present invention will become apparent from the accompanying description and disclosure.

SUMMARY OF THE INVENTION

In accordance with the teachings of the present invention, cellular polyurethanes are provided by effecting reaction of active hydrogen-containing compounds and polyisocyanates in the presence of a particular class of betaamino carbonyl compounds as catalytic components of the urethane-forming reaction mixture. The catalysts employed in the practice of this invention consist of carbon-bonded nitrogen, oxygen and hydrogen atoms and contain at least one tertiary nitrogen atom bonded to a carbon atom beta to the carbonyl group of an amido or carboxylic acid ester group. Tertiary nitrogen of the essential beta-amino carbonyl group is present in the molecule as a dialkylamino group or as a member of an N-heterocyclic nucleus which may contain additional hetero atoms such as oxygen or a second nitrogen atom. Overall, the beta-amino carbonyl compounds employed as described herein contain from 6 to 46 carbon atoms, from 1 to 4 nitrogen atoms and from 1 to 4 oxygen atoms. Except for carbonyl oxygen, the remaining atoms are joined through single bonds and thus the catalysts employed in the practice of this invention are free of multiple bonds between adjacent carbon atoms and adjacent carbon and nitrogen atoms.

The aforesaid essential structural characteristics of the beta-amino amides and beta-amino esters employed as described herein are conveniently expressed by the following general Formula I:

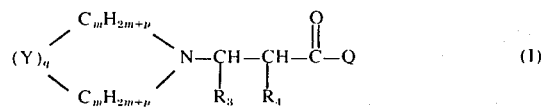

(I)

wherein, and as defined for the purpose of the entire specification:
Y is an oxygen or nitrogen atom and, when Y is nitrogen, the remaining valence thereof is satisfied by a bond to a second $-CH(R_3)CH(R_4)C(O)Q$ group;
$p$ and $q$ each has a value of zero or one, provided the sum p+q is one;
$m$ is an integer having a value from 1 to 4, provided $m$ is two when $q$ is one;
$R_3$ and $R_4$ each represents hydrogen or a lower alkyl group and may be the same as or different from one another; and
Q is a member of the group consisting of an alkoxy group ($-OR_7$) having from 1 to 8 carbon atoms, an N,N-dialkylamino group, $-N(R_5)(R_6)$, where $R_5$ and $R_6$ each represents a lower alkyl group, or a 2-(N,N-dialkylamino)ethoxy group, $-OCH_2CH_2N(R_5)(R_6)$, where $R_5$ and $R_6$ also represent lower alkyl radicals.

It is to be understood that the expression "lower alkyl" as used herein including the claims, denotes an alkyl radical having from one to four carbon atoms including linear and branched radicals (that is, radicals of the series, $C_mH_{2m+p}$, wherein $m$ is an integer from 1 to 4 and $p$ is one).

It has been discovered that the above-described beta-amino carbonyl compounds are useful as catalytic components in the manufacture of a wide variety of cellular urethanes including products ranging from flexible to rigid foams. They are effective activators when used as the sole nitrogen-bearing catalytic component of foam formulations, although their employment in combination with other tertiary amines is within the scope of the present invention. Especially effective in the catalysis of the water-isocyanate reaction, these beta-amino amides and esters are used with particular advantage in the manufacture of water-blown flexible foams, both molded and free-rise, including high-resilience foam. In addition to their versatility in this respect, they have the further highly desirable characteristic of low residual odor and thus allow for the formation of foam products essentially free of the post-cure odor associated with N-ethylmorpholine. Other beneficial properties include excellent mold-release characteristics, wide formulating latitude with repsect to concentration of tin co-catalysts, and ability to provide open-cell, porous foam from formulations containing an added flame-retarding agent.

It is noted that, as a class, beta-amino amides and esters including specific compounds employed in the practice of this invention are reported in the literature. As far as is known, however, their ability to function as catalysts in cellular urethane polymer formation has not been previously reported. On the other hand, certain of the beta-amino carbonyl compounds employed as catalysts in the practice of this invention are novel compositions. These include: (1) the heterocyclic beta-amino amides encompassed by Formula I, that is, those compounds in which $q$ is one and Q is an N,N-dialkylamino group; (2) 3-dialkylamino-N,N-dialkylamides wherein the alkyl groups bonded to amino nitrogen are different from those bonded to amido nitrogen; and (3) 3-dialkylamino-3-alkyl- N,N-dialkylamides wherein the various alkyl groups may be the same as or different from one another.

The present invention also relates to particular blends of the beta-amino carbonyl catalysts encompassed by Formula I with other tertiary amines, the use of such blends as mixed amine catalyst systems for cellular polyurethane formation, and to the cellular urethane polymers produced in the presence of the catalysts described herein.

DETAILED DESCRIPTION OF THE INVENTION AND PREFERRED EMBODIMENTS

A. The Beta-amino Carbonyl Catalysts

In generic Formula I, the sum p+q is one and thus when $q$ is zero, $p$ must have a value of one. In the latter event, each $C_mH_{2m+p}$ group shown in Formula I is a lower alkyl radical, designated herein as $R_1$ and $R_2$, and the indicated valence of carbon which would otherwise be in association with Y is satisfied by the additional hydrogen atom present when $p$ is one. The resulting saturated, acyclic beta-amino esters and amides have the more specific Formula II:

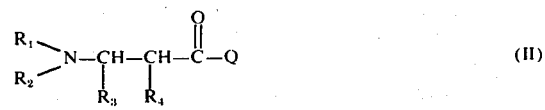

(II)

When Q is an alkoxy group, the catalysts encompassed by Formula II are alkyl beta-(dialkylamino)carboxylates having the following Formula II-A:

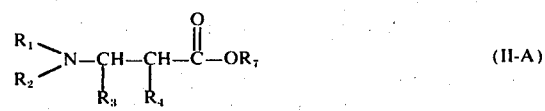

(II-A)

When Q of Formula II is a 2-(N,N-dialkylamino) ethoxy group, the catalysts are 2-(N,N-dialkylamino)ethyl 3-(N',N'- dialkylamino)carboxylates having the following Formula II-B:

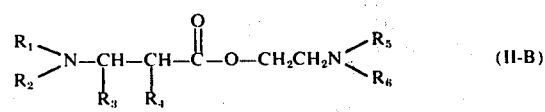

(II-B)

Further, when Q is an N,N-dialkylamino group, the catalysts encompassed by Formula II, are beta-(dialkylamino)-N,N- dialkylamides and have the structure shown by the following Formula II-C:

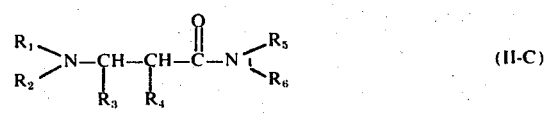

(II-C)

In addition to the saturated, acyclic esters and amides shown specifically by Formulas II-A, II-B and II-C, general Formula I also encompasses compounds wherein tertiary nitrogen is a member of a morpholine or piperazine nucleus. Such catalysts for use in the practice of this invention are depicted by the following Formulas III and IV, respectively:

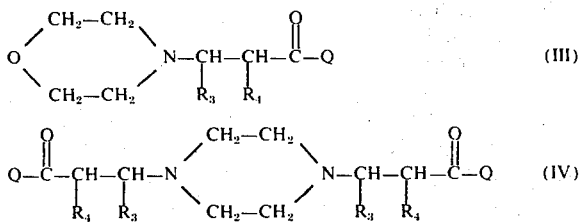

wherein the —C(O)Q group may be present as the ester groups shown in Formulas II-A and II-B or the amido group shown in Formula II-C. For example, when the Q radical of Formulas III and IV is a dialkylamino group, the respective compounds are 3-(N-morpholino)-N',N'-dialkylamides and N,N'-piperazonobis [3-(N'',N''-dialkylamides)]. These heterocyclic beta-amino amide catalysts are novel compounds and have the following more specific Formulas III-A and IV-A, respectively:

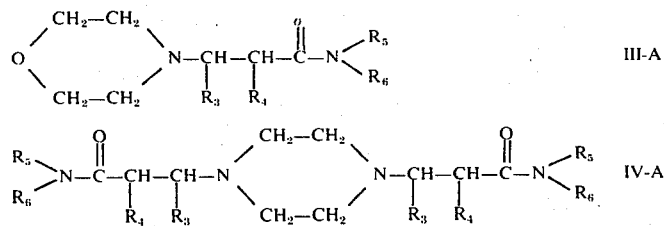

In the above formulas and as shown elsewhere in the present specification, $R_1$, $R_2$, $R_5$ and $R_6$ represent lower alkyl radicals, $R_3$ an $R_4$ may be hydrogen or lower alkyl, ad $R_7$ represents an alkyl radical having from 1 to 8 carbon atoms including linear and branched radicals and is more usually lower alkyl. It is to be understood that the lower alkyls represented by $R_1$, $R_2$, $R_5$ and $R_6$ and encompassed by $R_3$, $R_4$ and $R_7$, may be the same as or different from one another. The generally preferred catalysts for use in the practice of the present invention are those compounds wherein $R_1$, $R_2$, $R_5$ and $R_6$ are methyl or ethyl including any combination thereof and wherein at least one of $R_3$ and $R_4$ is hydrogen and the other is either hydrogen, methyl or ethyl.

In addition to the heterocyclic beta-amino amides encompassed by Formulas III-A and IV-A, particular acyclic compounds defined by Formula II-C are also novel compounds. Thus, when in Formula II-C, the alkyl groups represented by $R_1$ and $R_2$ are different from those represented by $R_5$ and $R_6$, the resulting unsymmetrically N-substituted 3-dialkylamino-N,N-dialkylamides are new compositions including those wherein $R_3$ and $R_4$ are hydrogen or alkyl, as previously defined. Also novel are the 3-dialkylamino-3-alkyl-N,N-dialkylamides, that is, those compounds encompassed by Formula II-C in which $R_3$ is limited to an alkyl group and $R_1$, $R_2$, $R_4$, $R_5$ and $R_6$ are as previously defined.

As between the various types of compounds employed in the practice of this invention, the catalysts encompassed by Formula II and III are generally preferred in that they also offer the processing advantage of being normally liquid materials, whereas the piperazine derived catalysts (Formula IV) are solids. From this standpoint, the acyclic catalysts having Formula II are especially preferred in that they are generally less viscous than the morpholine derivatives and thus can be handled and pumped more readily without dilution.

Typical examples of suitable catalysts for use in the formation of cellular urethane polymers in accordance with the teachings of this invention are the following compounds which, for clarity, are grouped according to the structural formulas within which they are specifically fall, all such catalysts being within the scope of generic Formula I.

Formula II-A
  methyl 3-(N,N-dimethylamino)propionate;
  ethyl 3-(N,N-dimethylamino)propionate;
  ethyl 3-(N,N-diethylamino)propionate;
  n-butyl 3-(N,N-diethylamino)propionate;
  i-butyl 3-(N,N-diamethylamino)butyrate;
  2-ethylhexyl 3-(N,N-dimethylamino)propionate;
  ethyl 2-methyl-3-(N,N-dimethylamino)propionate;
  propyl 3-(N,N-diethylamino) hexanoate;
  ethyl 3-(N-methyl-N-ethylamino-propionate; and
  methyl 3-butyl-3-(N,N-dimethylamino)heptanoate.

Formula II-B
  2-(N,N-dimethylamino)ethyl 3-(N',N'-dimethylamino)propionate;
  2-N,N-diethylamino)ethyl 3-(N',N'-dimethylamino)propionate;
  2-(N,N-diethylamino)ethyl 3(N',N'-dimethylamino)propionate;
  2-(N,N-dimethylamino)ethyl 2-methyl-3-(N',N'-dimethylamino)propionate;
  2-(N-methyl-N-ethylamino)ethyl 3-(N',N'-dimethylamino)propionate; and
  2-(N,N-diethylamino)ethyl 3-(N'-methyl-N'-ethylamino)butyrate.

Formula II-C
  3-dimethylamino-N,N-dimethylpropionamide;
  3-diethylamino-N,N-dimethylpropionamide;
  3-diethylamino-N,N-diethylpropionamide;
  3-dimethylamino-N,N-di-n-propylpropionamide;
  3-diethylamino-N,N-di-s-butylpropionamide;
  3-(N-methyl-N-ethylamino)-N'-n-butyl-N'-methylpropionamide;
  3-dimethylamino-2-methyl-N,N-dimethylpropionamide;
  3-dimethylamino-N,N-dimethylbutyramide;
  3-dimethylamino-N,N-dimethylpentamide; and
  3-diethylamino-N,N-dimethylhexamide.

Formula III including Formula III-A
  methyl 3-(N-morpholino)propionate;
  ethyl 3-(N-morpholino)propionate;
  ethyl 2-methyl-3-(N-morpholino) propionate;
  methyl 3-(N-morpholino)butyrate;
  2-(N,N-dimethylamino)ethyl 3-(N'-morpholino)propionate;
  3-(N-morpholino)-N',N'-dimethylpropionamide;
  3-(N-morpholino)-2-methyl-N',N'-dimethylpropionamide; and
  3-(N-morpholino)-N',N'-dimethylbutyramide.

Formula IV including Formula IV-A:
dimethyl 3-(N,N'-piperazino)dipropionate;
diethyl 3-(N,N'-piperazino)dipropionate;
di-2-(N,N-dimethylamino)ethyl 3-(N',N''-piperazino)dipropionate; and
N,N'-piperazino-bis[3-(N'',N''-dimethylpropionamide)].

The above-described beta-amino carbonyl compounds employed as catalysts in accordance with the present invention are readily prepared by a number of different types of reactions. A particularly facile method comprises the reaction of (A) secondary amines and (B) ester or amido derivatives of alpha,-beta-unsaturated carboxylic acids. With specific reference to Formula I, the overall reaction by which such compounds are provided is as follows:

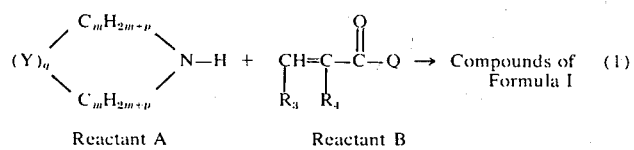

Consistent with the structure of the compounds encompassed by Formula I, Reactant A may be: a di(lower)alkylamine [$(R_1)(R_2)NH$] as typically illustrated by dimethylamine, diethylamine, di-n-propylamine, di-i-propylamine, dibutylamine, methylethylamine; or the heterocyclic amines, morpholine and piperazine. Also with reference to the structure of the compounds encompassed by Formula I, Reactant B may be: an alkyl ($R_7$) or a 2-(N,N-dialkylamino)ethyl [-$CH_2CH_2N(R_5)(R_6)$] ester derivative of an alpha,beta-unsaturated carboxylic acid having the formula, $CH(R_3)=C(R_4)C(O)OH$; or an alpha,beta-unsaturated N,N-di(lower)alkylamide having the formula, $CH(R_3)=C(R_4)C(O)N(R_5)(R_6)$. Typical examples of suitable unsaturated esters included within the definition of Reactant B are: methyl, ethyl, n-propyl, n-butyl, i-butyl, 2-ethylhexyl, 2-(N,N-dimethylamino)ethyl, 2-(N,N—diethylamino)ethyl and 2-(N-methyl-N-ethylamino)ethyl ester derivatives of acrylic, methacrylic, crotonic, 2-methylcrotonic (tiglic), 2-ethylpropenoic, 2-pentenoic, 2-ethyl-2-pentenoic, 2-hexenoic and 2-heptenoic acids. Illustrative of suitable unsaturated amide reactants encompassed by the definition of Reactant B are the corresponding amides containing the $CH(R_3)=C(R_4)C(O)$—nucleus of the aforesaid acids such as N,N-dimethyl-acrylamide, N,N-diethylacrylamide, N-methyl-N-ethylacrylamide, N,N-dimethylmethacrylamide, and N,N-dimethylcrotonamide.

Encompassed by the overall reaction of equation (1) is the direct 1:1 addition of the reactive H-N< group (or groups as in piperazine) of Reactant A across the double bond of Reactant B to form the corresponding beta-amino ester and amide adducts, as illustrated by the following equations (2)–(6):

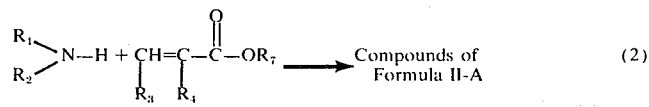

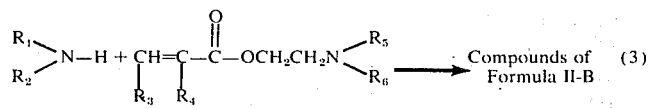

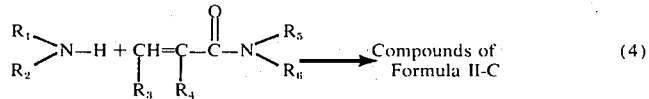

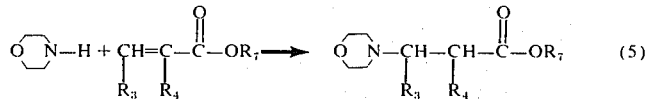

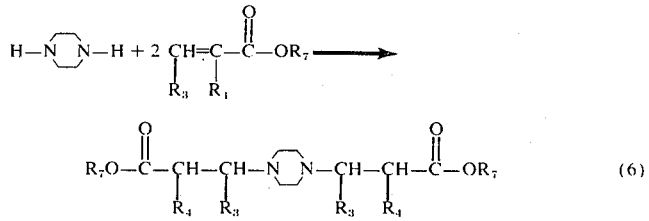

It is to be understood that replacement of the ester reactant shown in equation (5) with the unsaturated ester reactant shown in equation (3), provides the corresponding 2-(N,N-dialkylamino)ethyl 3-(N'-morpholino)-carboxylates, such compounds, as well as the ester products of equation (5), being encompassed by Formula III. It also is to be understood that when morpholine is reacted with the unsaturated amide reactants shown in equation (4), the products are the corresponding 3-(N-morpholino)-N',N'-dialkylamides which are also encompassed by Formula III and defined specifically by Formula III-A. Similarly, when the ester reactant shown in equation (6) is replaced with the unsaturated ester reactant shown in equation (3), the corresponding di-2-(N,N-dialkylamino)ethyl 3-(N',N''-piperazino)dicarboxylates are provided, such products as well as those of equation (6) being encompassed by Formula IV. Likewise, reaction of 1,4-piperazine with the alpha,beta-unsaturated amides shown in equation (4) provides the corresponding N,N'-piperazino-bis[3-(N'',N''-dialkylamides)] which are also encompassed by Formula IV and defined specifically by Formula IV-A.

The addition reactions illustrated by equations (2)–(6) are effected at temperatures within the range from about minus 15° C. to about 120° C. and proceed at satisfactory rates at ambient or substantially atmospheric pressures. Reactions based on dimethylamine are generally more highly exothermic than those based on higher homologues and thus are usually effected at the lower temperatures within the aforesaid range. As required, temperature control is achieved in conventional manner such as by cooling or appropriate adjustment of the rate at which the reactants are fed to the reactor. The relative proportions of reactants are such to at least satisfy the indicated stoichiometric requirements of the addition, although either reactant may be employed in excess of stiochiometry to favor completion of the reactions. Usually, no more than a 125 percent molar excess of either reactant is employed.

As illustrated by the reaction of equation (4) the beta-amino amide catalysts can be prepared by the addition of secondary amines to alpha,beta-unsaturated, N,N-dialkylamides. These catalysts can also be provided by the following application of the overall reaction of equation (1):

Equation 7

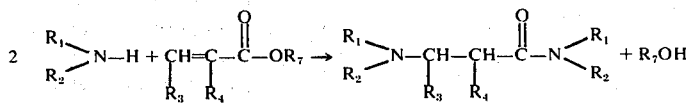

This reaction may be viewed as an extension of the addition reaction of equation (2) in that it proceeds through intermediate formation of the alkyl beta(dialkylamino)carboxylates (Formula II-A) followed by amidation which is an endothermic reaction. Thus, for any given combination of dialkylamine and alkyl alpha,-beta-unsaturated carboxylate reactants, higher severity conditions are employed when it is desired to recover the amidated product. Generally, the amidation reactions encompassed by equation (7) are effected at temperatures within the range from about 100° C. to about 250° C. and at elevated pressures from about 50 to about 1200 p.s.i.g. In order to favor completion of the reaction, the amine reactant is preferably employed in excess of stoichiometry, amounts up to about a 100 percent molar excess usually being suitable for this purpose. The reaction of equation (7) may be carried out in batchwise fashion by initially charging total reactants to the reactor and applying the aforesaid high temperature-elevated pressure conditions. Alternatively, the reaction may be carried out as an essentially two-stage process. In accordance with the latter method, a portion of total amine reactant is fed to the unsaturated ester under the less severe addition reaction conditions to form the 1:1 adduct, followed by reaction of the intermediate with the remainder of amine under the aforesaid more severe amidation conditions. It is to be understood that the amine fed to the first stage may be different from that fed to the second stage, thereby providing amine and amido groups having a different combination of $R_1$ and $R_2$ groups, that is, compounds encompassed by Formula II-C wherein the alkyl groups represented by $R_1$ and $R_2$ are different from the alkyls represented by $R_5$ and $R_6$.

In order to minimize formation of by-products by retro-addition reactions and hydrolysis of ester reactants as well as ester products, it is recommended practice to effect the above-described reactions under anhydrous or substantially anhydrous conditions. Thus, the reaction media should contain less than about 5 weight percent water, expressed on the basis of amine reactant. Formation of by-products such as alpha,beta-unsaturated amides may also be formed during the reactions. Minor amounts of compounds which have an inhibiting effect on polymerization of such by-products may be added to the reaction media. Illustrative of suitable inhibitors are phenothiazine, p-methoxyphenol and hydroquinone. The reaction media may also contain solvents or diluents such as, for example, ethanol, butanol, diisopropyl ether, dioxane and other such compounds which are inert under the reaction conditions.

The technique by which the beta-amino amide and ester catalysts are recovered depends largely on their physical nature and properties. Thus, the normally liquid products encompassed by Formulas II and III are recovered by distillation or as residue products remaining after removal of more volatile components. Recovery as residue products is usual practice in the case of the higher molecular weight compounds such as the morpholine-derived compounds and acyclic compounds in which the various alkyl groups are propyl and butyl. The piperazine-derived catalysts are recovered by conventional liquid-solid separation techniques.

The effectiveness of the beta-amino carbonyl compounds as catalysts for cellular urethane manufacture as described herein, does not depend on their use in a rigorously pure state. Included within the scope of the present invention, therefore, is the use of the catalysts as either substantially pure compounds, in combination with one another, or in association with impurities which may form during their manufacture.

B. THE FOAM FORMULATIONS

In producing cellular urethane polymers in accordance with the teachings of this invention, the reaction mixture or foam formulation contains, in addition to the beta-amino carbonyl catalysts, an organic polyisocyanate and an active hydrogen-containing organic compound having an average of at least two and usually not more than eight active hydrogen atoms present as hydroxyl groups. Such organic polyol reactants include compounds consisting of carbon, hydrogen and oxygen as well as compounds which contain these elements in combination with phosphorus, halogen and/or nitrogen. Suitable classes of organic polyol reactants for use in the method of this invention are polyether polyols, polyester polyols, polylactone polyols, nitrogen-containing polyols, phosphorus-containing polyols, phenolic-based polyols, and polymer-polyols produced by polymerizing an ethylenically unsaturated monomer in one of the aforesaid polyols in the presence of a free radical initiator.

It is well known to the polyurethane art that the particular polyol reactant or combination of polyols employed depends upon the end-use of the polyurethane product which in turn determines whether the product is to be provided as a flexible, semi-flexible or rigid material. For this purpose, the polyol reactant is usually characterized by its hydroxyl number which is determined by and defined as the number of milligrams of potassium hydroxide required for the complete neutralization of the hydrolysis product of the fully acetylated derivative prepared from 1 gram of polyol or mixture of polyols. The hydroxyl number is also defined by the following equation which reflects its relationship with the functionality and molecular weight of the polyol reactant:

$$OH = \frac{56.1 \times 1000 \times f}{M.W.}$$

wherein
OH = hydroxyl number of the polyol;
f = average functionality, that is, average number of hydroxyl groups per molecule of polyol; and
M. W. = average molecular weight of the polyol. The beta-amine carbonyl compounds described herein are suitably employed as catalytic components of foam formulations containing polyols having hydroxyl numbers from about 20 to about 1000. In producing flexible foams, polyols having relatively low hydroxyl numbers such as from about 20 to about 100 are generally employed. In producing semi-flexible materials, the hydroxyl number is usually from about 100 to about 300. Polyols having relatively high hydroxyl numbers of from about 300 to about 1000 are used in rigid foam formulations.

Suitable polyethers that can be employed include linear and branched polyethers preferably having a plurality of ether linkages and containing at least two hydroxyl groups and being substantially free from functional groups other than hydroxyl. For convenience, this class of polyether polyols are referred to herein as Polyol I. These compounds include alkylene oxide adducts of water such as polyethylene glycols having average molecular weights from about 200 to about 600, polypropylene glycols having average molecular weights from about 400 to about 2000, and polyoxyalkylene polyols having a combination of different alkylene oxide units. Other suitable polyols encompassed within the definition of Polyol I are the alkylene oxide adducts of polyhydric organic initiators, the nature of which determines the average hydroxyl functionality of the polyoxyalkylated product. Illustrative of suitable polyhydric organic initiators are the following which can be employed individually or in combination with one another: (1) diols such as ethylene glycol, diethylene glycol, propylene glycol, 1,5-pentanediol, hexylene glycol, dipropylene glycol, trimethylene glycol, 1,2-cyclohexanediol, 3-cyclohexene-1,1-dimethanol and 3,4-dibromocyclohexane-1,1-dimethanol; (2) triols such as glycerol, 1,2,6-hexanetriol, 1,1,1-trimethylolethane, 1,1,1-trimethylolpropane, 3-(2-hydroxyethoxy)- and 3-(2-hydroxypropoxy)-1,2-propanediols, 2,4-dimethyl-2-(2-hydroxyethoxy)methyl-pentanediol-1,5, 1,1,1-tris[(2-hydroxyethoxy)methyl]ethane and 1,1,1-tris[(2-hydroxypropoxy)methyl]propane; (3)tetrols such as pentaerythritol; (4) pentols, hexols, heptanols and octanols such as glucose, sorbitol, bis(2,2,2-trimethylol)ethyl ether, alpha-methyl glucoside, sucrose, mannose and galactose; (5) compounds in which hydroxyl groups are bonded to an aromatic nucleus such as resorcinol, pyrogallol, phloroglucinol, di-, tri- and tetra-phenylol compounds such as bis(p-hydroxyphenyl)methane and 2,2-bis(p-hydroxyphenyl)propane; and (6) alkylene oxide adducts of the aforesaid initiators such as propylene or ethylene oxide adducts of glycerol having a relatively low average molecular weight up to about 600. Particularly useful in the preparation of flexible foams generally are polyether polyols having an average hydroxyl functionality of from about 2.1 to about 4. Such polyols are provided by the employment of either trihydric or tetrahydric starters, mixtures thereof, or appropriate mixtures containing diol starters. The more highly functional polyether polyols are usually employed in providing the semi-flexible and rigid foams.

The above-described polyether polyols are normally liquid materials and, in general, are prepared in accordance with well known techniques comprising the reaction of the polyhydric starter and an alkylene oxide in the presence of an oxyalkylation catalyst. Usually, the catalyst is an alkali metal hydroxide such as, in particular, potassium hydroxide. The oxyalkylation of the polyhydric initiator is carried out at temperatures ranging from about 90°C. to about 150°C. and usually at an elevated pressure up to about 200 p.s.i.g., employing a sufficient amount of alkylene oxide and adequate reaction time to obtain a polyol of desired molecular weight which is conveniently followed during the course of the reaction by standard hydroxyl number determinations, as defined above. The alkylene oxides most commonly employed in providing the reactants encompassed by Polyol I, are the lower alkylene oxides, that is, compounds having from 2 to 4 carbon atoms including ethylene oxide, propylene oxide, butylene oxides (1,2- or 2,3-) and combinations thereof. When more than one type of oxyalkylene unit is desired in the polyol product, the alkylene oxide reactants may be fed to the reaction system sequentially to provide polyoxyalkylene chains containing respective blocks of different oxyalkylene units or they may be fed simultaneously to provide substantially random distribution of units. Alternatively, the polyoxyalkylene chains may consist essentially of one type of oxyalkylene unit such as oxypropylene capped with oxyethylene units.

A second class of polyols that are suitable for use in preparing polyurethane foams in accordance with the present invention are polymer/polyols which, for convenience, are referred to herein as Polyol II. Such reactants are produced by polymerizing one or more ethylenically unsaturated monomers dissolved or dispersed in any of the other types of organic polyol reactants described herein, in the presence of a free radical catalyst. Especially suitable as the substrate polyols for producing such compositions are any of the above-described polyether glycols encompassed by the definition of Polyol I. Illustrative of suitable ethylenically unsaturated monomers are vinyl compounds having the general formula,

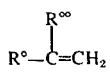

where: R° is hydrogen, methyl or any of the halogens (i.e., fluorine, chlorine, bromine or iodine); and R^∞ is R°, cyano, phenyl, methyl-substituted phenyl, carboalkoxy, or alkenyl radicals having from 2 to 6 carbon atoms such as vinyl, allyl and isopropenyl groups. Typical examples of such polymerizable monomers are the following which may be employed individually or in combination: ethylene, propylene, acrylonitrile, methacrylonitrile, vinyl chloride, vinylidene chloride, styrene, alpha-methylstyrene, methyl methacrylate, and butadiene. These and other polymer/polyol compositions which are suitably employed either individually or in combination with Polyol I are those described in British Pat. No. 1,063,222 and U.S. Pat. Nos. 3,304,273, 3,523,093 and 3,383,351, the disclosures of which are incorporated herein by reference. Such compositions are prepared by polymerizing the monomers in the polyol at a temperature between about 40° C. and about 150° C. employing any free radical-generating initiator including peroxides, persulfates, percarbonates, perborates and azo compounds. Illustrative of suitable initiators are: hydrogen peroxide, dibenzoyl peroxide, benzoyl hydroperoxide, lauroyl peroxide and azobis(isobutyronitrile).

The polymer/polyol compositions usually contain from about 5 to about 50, and more usually from about 10 to about 40, weight percent of the vinyl monomer or monomers polymerized in the polyol. Especially effective polymer/polyols are those having the following composition:

A. from about 10 to about 30 weight percent of a copolymer of (1) acrylonitrile or methacrylonitrile, and (2) styrene or alpha-methylstyrene, the said copolymer containing from about 50 to 75 and from about 50 to 25 weight percent of monomeric units of (1) and (2), respectively; and B. from about 90 to about 70 weight percent of one or more of the polyols encompassed by Polyol I as the medium in which said component (A) is polymerized, the trifunctional polyols such as alkylene oxide adducts of glycerol being especially suitable. These polymer/polyol compositions containing components (A) and (B) are the subject of copending U.S. application Ser. No. 176,317, filed Aug. 30, 1971, in the name of David C. Priest.

Other types of suitable polyol reactants for use in producing cellular polyurethanes as described herein are polyester polyols provided as the reaction products of: (1) a polyfunctional organic carboxylic acid, and (2) one or more of the aforesaid polyether polyols or one or more of the aforesaid polyhydric organic compounds which are reacted with alkylene oxide to produce such polyether polyols. Among the suitable polycarboxylic acids that can be employed in producing such polyester polyols are: the aliphatic acids which are usually free of reactive unsaturation such as ethylenic and acetylenic groups, such as, for example, succinic acid, adipic acid, sebacic acid, azelaic acid, glutaric acid, pimelic, malonic, and suberic acids; cycloaliphatic acids such as chlorendic acid; and aromatic poly-basic acids such as phthalic, terephthalic, isophthalic acids and the like.

Also contemplated for use as a polyol reactant of the foam formulations employed in the practice of this invention are nitrogen-containing polyols. Such polyols include lower alkylene oxide adducts of the following amines which may be employed individually or in combination: primary and secondary polyamines such as ethylenediamine, diethylenetriamine and toluenediamine; and aminoalkanols such as ethanolamine, diethanolamine, triethanolamine and triisopropanolamine. Also suitable are mixed starters containing one or more of the aforesaid polyfunctional amines, aniline, and/or one or more of the polyhydric initiators employed to produce Polyol I such as dipropylene glycol, glycerol and sucrose. Also illustrative of suitable nitrogen-containing polyols are aniline/formaldehyde and aniline/phenol/formaldehyde condensation products. Such amine-based polyols are usually employed in rigid foam formulations.

Other suitable polyols for use in producing polyurethane foams as described herein are: lactone-based polyols prepared by reacting a lactone such as epsilon-caprolactone, or a mixture of epsilon-caprolactone and an alkylene oxide, with a polyfunctional initiator such as a polyhydric alcohol, an amine, or an aminoalcohol; phosphorus-containing polyols such as the alkylene oxide adducts of phosphoric acid, polyphosphoric acids such as tri- and tetra-phosphoric acids, organo-substituted phosphoric acids such as benzenephosphoric acid; and other polyol reactants known to the polyurethane art.

The beta-amino carbonyl compounds described herein are used with particular advantage as catalysts in the manufacture of high-resilience flexible foam. Such foams usually have a resiliency of from about 55 to about 70 percent, as measured by standard test procedure ASTM D-1564-69. In accordance with a preferred embodiment of this aspect of the present invention, the beta-amino carbonyl compounds are employed as catalytic components of high-resilience foam formulations wherein at least 40 weight percent of the total polyol content is constituted of a polyether triol having the following additional characteristics: (a) an average primary hydroxyl content of at least 40 mole percent (or no more than 60 mole percent of the less reactive secondary hydroxyl groups); and (b) an average molecular weight of from about 2000 to about 8000. For convenience, this particular class of polyols are referred to herein as Polyol I-A. Preferably, such polyether triols for use as components of high-resilience formulations contain from about 60 to about 90 mole percent of primary hydroxyl groups and have an average molecular weight of from about 4000 to about 7000. Consistent with their trifunctionality and the aforesaid respective ranges of molecular weight, such polyether triols have hydroxyl numbers from 84 to 21, preferably from 42 to 24. These highly reactive polyether triols are provided by oxyalkylation of one of the aforesaid trihydric starters such as glycerol, with propylene oxide and ethylene oxide. Usually, the total ethylene oxide content of the polyether triols encompassed by the definition of Polyol I-A is between about 7 and about 20 weight percent, expressed on the basis of total alkylene oxide fed during the oxyalkylation reaction. The high primary hydroxyl content is introduced by capping of the polyoxyalkylene chains with at least a portion of the total ethylene oxide feed.

In providing high-resilience foams, the polyether triols included within the definition of Polyol I-A may be used as essentially the sole type of polyol in the formulation or they may be employed in combination with other polyols to control the degree of softness or firmness of the foam and to vary the load-bearing properties. For example, when softer grade high-resilience foams are desired, Polyol I-A may be used in combination with polyether diols such as the above-described lower alkylene oxide adducts of a dihydric initiator such as dipropylene glycol. When firm grades of high-resilience foams having enhanced load-bearing properties are desired, Polyol I-A is used in combination with up to about 60 parts by weight per 100 parts by weight of total polyol reactant (p.p.h.p) of a polymer/polyol encompassed within the definition of Polyol II. In this latter respect, particularly effective mixtures of polyols are those containing:

1. from about 40 to about 80 p.p.h.p. of the polyether triols, designated hereinabove as Polyol I-A; and 2. from about 60 to about 20 p.p.h.p. of polymer/polyols, designated herein as Polyol II-A, prepared by the in situ polymerization of a monomer mixture containing from about 50 to about 75 weight percent of acrylonitrile and from about 50 to about 25 weight percent of styrene, in Polyol I-A, the said monomer mixture constituting from about 10 to about 30 weight percent of the combined weight of the monomers and Polyol I-A.

The polyisocyanates used in the manufacture of polyurethanes are known to the art and any such reactants are suitably employed in producing polyurethane foams in the presence of the beta-amino carbonyl catalysts described herein. Among such suitable polyisocyanates are those represented by the general formula:

$$Q'(NCO)_i$$

wherein: $i$ has an average value of at least two and is usually no more than six, and $Q'$ represents an aliphatic, cycloaliphatic or aromatic radical which can be an unsubstituted hydrocarbyl group or a hydrocarbyl group substituted, for example, with halogen or alkoxy. For example, $Q'$ can be an alkylene, cycloalkylene, arylene, alkyl-substituted cycloalkylene, alkarylene or aralkylene radical including corresponding halogen- and alkoxy-substituted radicals. Typical examples of polyisocyanates for use in preparing the polyurethanes of this invention are any of the following including mixtures thereof: 1,6-hexamethylene diisocyanate, 1,4-tetramethylene diisocyanate, bis(2-isocyanatoethyl)-fumarate, 1-methyl-2,4-diisocyanatocyclohexane, bis(4-isocyanatophenyl)methane, phenylene diisocyanates such as 4-methoxy-1,4-phenylenediisocyanate, 4-chloro-1,3-phenylenediisocyanate, 4-bromo-1,3-phenylenediisocyanate, 5,6-dimethyl-1,3-phenylenediisocyanate, 2,4-tolylene diisocyanate, 2,6-tolylene diisocyanate, crude tolylene diisocyanates, 6-isopropyl-1,3-phenylenediisocyanate, durylene diisocyanate, triphenylmethane-4,4',4''-triisocyanate, and other organic polyisocyanates known to the polyurethane art. Other suitable polyisocyanate reactants are ethylphosphonic diisocyanate and phenylphosphonic diisocyanate. Of the aforesaid types of polyisocyanates, those containing aromatic nuclei are generally preferred.

Also useful as the polyisocyanate reactant are polymeric isocyanates having units of the formula:

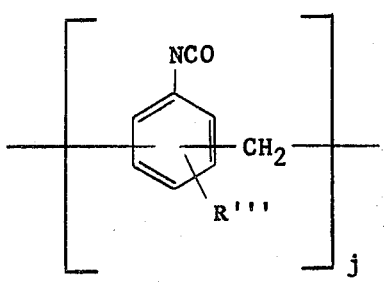

wherein $R'''$ is hydrogen and/or lower alkyl and $j$ has an average value of at least 2.1. Usually, the lower alkyl radical is methyl and $j$ has an average value no higher than about 4. Particularly useful polyisocyanates of this type are the polyphenylmethylene polyisocyanates produced by phosgenation of the polyamine obtained by acid-catalyzed condensation of aniline with formaldehyde. Polyphenylmethylene polyisocyanates of this type are available commercially under such trade names as PAPI, NIAX Isocyanate AFPI, Mondur MR, Isonate 390P, NCO-120, Thanate P-220, NCO-10 and NCO-20. These products are low viscosity (50-500 centipoises at 25°C.) liquids having average isocyanato functionalities in the range of about 2.25 to about 3.2 or higher, and free —NCO contents of from about 25 to about 35 weight percent, depending upon the specific aniline-to-formaldehyde molar ratio used in the polyamine preparation.

Also useful as polyisocyanate reactants are polymeric tolylene diisocyanates obtained as residues from the manufacture of the diisocyanates and having a free —NCO content of from about 30 to about 50 weight percent. Other useful polyisocyanate reactants are combinations of diisocyanates with polymer isocyanates containing more than two isocyanate groups per molecule. Illustrative of such combinations are: a mixture of 2,4-tolylene diisocyanate, 2,6-tolylene diisocyanate and the aforesaid polyphenylmethylene polyisocyanates and/or the aforementioned residue products.

Of the aforesaid polyisocyanates, those employed with particular advantage in providing high-resilience foams are mixtures containing from about 60 to about 90 weight percent of the isomeric tolylene diisocyanates and from about 40 to about 10 weight percent of the polyphenylmethylene polyisocyanates, in order to enhance the average —NCO functionality and thus the reactivity of the reaction mixture. When the high-resilience formulations contain diisocyanates as essentially the sole source of reactive —NCO, it is often desirable to include minor amounts, such as up to about 1.5 p.p.h.p., or cross-linking agents. Suitable additives for this purpose are diethanolamine, methyldiethanolamine and triethanolamine.

On a combined basis, the polyol reactant and organic polyisocyanate usually constitute the major proportion by weight of the polyurethane-forming reaction mixture. In general, the polyisocyanate and polyol reactants are employed in relative amounts such that the ratio of total —NCO equivalents to total active hydrogen equivalent (of the polyol and any water, when used) is from 0.8 to 1.5, usually from 0.9 to 1.20, equivalents of —NCO per equivalent of active hydrogen. This ratio is known as the Isocyanate Index and is often also expressed as a percent of the stoichiometric amount of polyisocyanate required to react with total active hydrogen. When expressed as a percent, the Isocyanate Index may be from 80 to 150, and is usually within the range from about 90 to about 120. More usually, the Isocyanate Index is no more than about 115.

The beta-amino carbonyl catalysts may be employed individually or in combination with one another and are present in the foam formulation in catalytically effective amounts. Thus, the total concentration thereof may vary over a relatively wide range such as from about 0.01 to about 5 or more parts by weight (exclusive of any carrier solvents or other additives) per 100 parts by weight of the total polyol reactant contained in the reaction mixture. Usually, this catalytic component is present in an amount from about 0.05 to about 3.0 p.p.h.p. In flexible foam formulations, it is usually adequate to employ the beta-amino carbonyl catalysts in an amount up to about one p.p.h.p., whereas in rigid formulations, higher concentrations are usually used.

The beta-amino carbonyl catalysts may be employed as the sole type of amine catalyst of the foam formulations described herein or they may be employed in combination with one or more tertiary amines conventionally employed as catalysts in producing polyurethanes. Such additional catalysts include amines consisting of carbon, hydrogen and nitrogen, as well as amines consisting of these three elements and oxygen wherein oxygen is present solely as ether or hydroxyl groups. Although these auxiliary amine catalysts can contain up to 24 carbon atoms, the more commonly employed compounds contain no more than 12 carbons. Illustrative of such tertiary amines for use in combination with the beta-amino carbonyl catalysts are: trimethylamine; triethylamine; tributylamine; N,N,N',N'-tetramethylethylenediamine; N,N,N',N'-tetramethyl-1,3-butanediamine; N,N-dimethylcyclohexylamine; N,N-dimethylbenzylamine; bis[2-(N,N-dimethylamino)alkyl]ethers such as bis[2-(N,N-dimethylamino)ethyl]ether; triethylenediamine; N-methylmorpholine; N-ethylmorpholine; N-(2-hydroxyethyl)-piperazine; N-methyldiethanolamine; N,N-dimethylethanolamine; and other such conventional tertiary amine polyurethane catalysts. Of the aforesaid tertiary amines, those containing reactive hydroxyl are often used to serve the additional function of cross-linking agents. Such alkanolamines are often used in the manufacture of rigid foams, or to enhance cross-linking density of high-resilience foams based on diisocyanates.

When used, the supplementary tertiary amine catalysts may be present in the foam formulation in an amount within the aforesaid ranges defined with respect to the beta-amino carbonyl catalysts, although usually the total amount of supplementary amine is no more than about one p.p.h.p. It is to be understood that the beta-amino carbonyl catalyst and the supplementary tertiary amine, when used, may be added to the formulation as separate streams or in preblended form.

Illustrative of suitable blended catalysts provided by the present invention and which are especially useful as components of water-blown, flexible foam formulations including high-resilience systems, are those containing from about 10 to about 90 weight percent of the beta-amino carbonyl compounds and correspondingly from about 90 to about 10 weight percent of either bis[2-(N,N-dimethylamino)ethyl]ether, triethylenediamine, or the bis-amino ether plus triethylenediamine. It is to be understood that the said weight percentages are based on the total weight of the blended catalysts, exclusive of carrier solvents or other additives. These blends are added to the foam formulations in an amount sufficient to provide the beta-amino carbonyl catalyst and auxiliary amine within the aforesaid respective ranges of concentration, that is, between about 0.01 and about 5 p.p.h.p.

From the standpoint of providing an effective catalyst system, the beta-amino carbonyl catalyst may be used, as included in the foregoing description, in combination with N-alkylmorpholines such as N-ethylmorpholine. The latter compound is presently used in commercial practice in relatively high concentrations (up to about 2.0 p.p.h.p.) as a catalytic component of molded high-resilience formulations in order to provide foams having good mold-release characteristics. In view of the present discovery that such foams can be produced by employing the beta-amino carbonyl catalysts described herein without the necessity of using N-ethylmorpholine, the latter catalyst may be completely eliminated, thereby avoiding the obnoxious residual foam odor associated therewith. It is to be understood, however, that N-ethylmorpholine may be used as a component of the foam formulations described herein without departing from the scope of this invention. When used, the level of such N-alkylmorpholine catalysts is desirably kept to a minimum such as no more than about 0.30 p.p.h.p.

It is to be understood that the beta-amino carbonyl catalysts employed in accordance with the present invention, as well as blends based thereon, may be introduced to the foam formulations in undiluted form or as solutions in suitable carrier solvents such as diethylene glycol, dipropylene glycol and hexylene glycol. The supplementary amine catalysts are also often employed in such carrier solvents.

Other useful carrier solvents for the catalysts described herein are lower alkylene oxide adducts of monohydric or polyhydric starters such as butanol, dipropylene glycol and glycerol. Such solvents (or diluents) generally include adducts containing from about 3 to about 30 oxyethylene or oxypropylene units, mixtures of such adducts, as well as adducts provided by reaction of the starter with ethylene oxide and propylene oxide, fed either as a mixed feed or sequentially. Among the suitable organic carrier solvents of this type are the ethylene oxide-propylene oxide adducts of butanol having the average formula, $C_4H_9(OC_3H_6)_u(OC_2H_4)_sOH$, wherein $s$ and $u$ may each have an average value from about 3 to about 30. Preferably, the values of $s$ and $u$ are such that the average molecular weight of these fluids is not substantially greater than about 2000 and the oxyethylene content is from about 20 to about 80 weight percent, based on total polyoxyalkylene content. Usually, the weight percent of oxyethylene is about the same as the weight percent of oxypropylene.

Also included within the scope of the present invention is the use of the beta-amino carbonyl catalysts in combination with organic surfactants. When used, the organic surfactant is usually a non ionic surfactant such as: the polyoxyalkylene ethers of higher alcohols having from 10 to 18 carbon atoms including mixtures thereof; and polyoxyalkylene ethers of alkyl-substituted phenols in which the alkyl group can have from 6 to 15 carbon atoms. The length of the ether chain is such that appropriate hydrophilic character is provided to balance the hydrophobic portion derived from the alcohol or phenol and render the compound miscible with water. The chain may contain oxyethylene units either as essentially the sole type of unit or oxyethylene in combination with a minor amount of oxypropylene. It is preferred that the hydrophilic portion of the non ionic surfactants be composed essentially of oxyethylene monomeric units. Usually the average number of such $-OC_2H_4-$ units ranges from about 4 to about 20, although upwards of 30 such units can also be present.

Typical examples of non ionic surfactants which can be used in combination with the beta-amino carbonyl catalysts employed in the practice of this invention are the adducts produced by reaction of from about 4 to about 30 moles of ethylene oxide per mole of any of the following hydrophobes including mixtures thereof: n-undecyl alcohol, myristyl alcohol, lauryl alcohol, trimethyl nonanol, tridecyl alcohol, pentadecyl alcohol, cetyl alcohol, oleyl alcohol, stearyl alcohol, nonylphenol, dodecylphenol, tetradecylphenol, and the like. Especially suitable for use as the carrier medium for the beta-amino carbonyl catalysts described herein are the ethylene oxide adducts of nonylphenol having the average composition, $C_9H_{19}-C_6H_4-(OC_2H_4)_h-OH$, wherein $h$ has an average value from about 4 to about 20, inclusive of whole and fractional numbers, such as 6, 9, 10.5 and 15.

The above-described solution compositions may contain from about 10 to about 90 weight percent of total beta-amino carbonyl catalyst (inclusive of supplementary tertiary amine catalyst, when used), based on the combined weight of catalyst, solvent and/or organic surfactant, depending upon whether the catalyst is employed in combination with either one or both of the solvent and organic surfactant.

It is often desirable to include as a further component of the foam formulation a minor amount of certain metal catalysts, particularly organic derivatives of tin including stannous and stannic compounds. Such metal co-catalysts are well known to the art and are usually employed in producing polyether polyol-based polyurethanes. Illustrative of suitable organic tin compounds are the following which may be employed individually or in combination: stannous salts of carboxylic acids such as stannous octoate, stannous oleate, stannous acetate and stannous laurate; dialkyltin dicarboxylates such as dibutyltin dilaurate, dibutyltin diacetate, dilauryltin diacetate, dibutyltin di(2-ethylhexanoate) and other such tin salts as well as dialkyltin oxides, trialkyltin oxides, tin mercaptides such as, for example, di-n-octyl tin mercaptide, and the like. When used, the amount of such metal co-catalysts ranges from about 0.001 to about 2 parts by weight per 100 parts by weight of total polyol reactant. In flexible foam formulations, the metal co-catalyst is preferably used in an amount from about 0.01 to about 1.6 p.p.h.p., and most preferably in an amount no more than about 0.5 p.p.h.p.

Foaming is accomplished by the presence in the reaction mixture of varying amounts of a polyurethane blowing agent such as water which, upon reaction with isocyanate, generates carbon dioxide in situ, or through the use of blowing agents which are vaporized by the exotherm of the reaction, or by a combination of the two methods. These various methods are known in the art. Thus, in addition to or in place of water, other blowing agents which can be employed in the process of this invention include methylene chloride, liquefied gases which have boiling points below 80°F. and above −60°F., or other inert gases such as nitrogen, carbon dioxide added as such, methane, helium and argon.

Suitable liquefied gases include aliphatic and cycloaliphatic fluorocarbons which vaporize at or below the temperature of the foaming mass. Such gases are at least partially fluorinated and may also be otherwise halogenated. Fluorocarbon agents suitable for use in foaming formulations of this invention include: trichloromonofluoromethane; dichlorodifluoromethane: 1,1-dichloro-1-fluoroethane; 1,2,2-trifluoro-1,1,2-trichloroethane; 1,1,1-trifluoro-2-fluoro-3,3-difluoro-4,4,4-trifluorobutane; hexafluorocyclobutene; and octafluorocyclobutane. Another useful class of blowing agents include thermally-unstable compounds which liberate gases upon heating, such as N,N'-dimethyl-N,N'-dinitrosoterephthalamide, and the like.

Generally, the blowing agent is employed in an amount from about 1 to about 45 parts by weight per 100 parts by weight of total polyol reactant, the particular blowing agent and amount thereof depending upon the type of foam product desired. Flexible foam formulations including those which favor formation of high-resilience foam, are most usually water blown, although a minor proportion such as up to about 10 weight percent of total blowing agent may be constituted of a fluorocarbon such as trichlorofluoromethane. Flexible foam formulations usually contain no more than about 10 p.p.h.p. of water. For rigid formulations, blowing action is usually supplied employing a fluorocarbon in a relatively high proportion such as from about 10 to about 45 p.p.h.p., either as the sole type of agent or in combination with a minor amount of water such as up to about 10 weight percent of total blowing agent. The selection and amount of blowing agent in any particular foam formulation is well within the skill of the cellular polyurethane art.

In producing cellular polyurethanes in accordance with the method of this invention, a minor amount of an organosilicone surfactant may also be present as an additional component of the polyurethane-forming reaction mixture. When used, such surfactants are usually present in amounts up to about 5 parts by weight per 100 parts by weight of total polyol reactant.

Among the suitable classes of surfactant are the polysiloxane-polyoxyalkylene block copolymers wherein the respective blocks are joined through silicon-to-carbon or silicon-to-oxygen-to-carbon bonds and the respective polyoxyalkylene blocks are bonded to different silicon atoms of the polysiloxane backbone to form a comb-like structure. Usually, the polysiloxane blocks are trialkysiloxy-endblocked. In addition to the siloxy units to which the pendant polyoxyalkylene chains are bonded, the polysiloxane backbone is formed of difunctional siloxy units wherein the respective two remaining valences of silicon are satisfied by bonds to organic radicals. Illustrative of such organic radicals are the hydrocarbyl groups having from 1 to 12 carbon atoms including alkyl, aryl, aralkyl, bicycloheptyl and halogen-substituted derivatives of such groups. The polyoxyalkylene blocks are usually constituted of oxyethylene units, oxypropylene units or a combination of such units, and the polyoxyalkylene chains are hydroxyl-terminated or capped with a monovalent organic group such as alkyl, aryl, aralkyl, acyl, carbamyl and the like. Especially useful as stabilizers of flexible polyether-based polyurethane foams are the block copolymers described in U.S. Pat. No. 3,505,377, an application for reissue of which was filed on Nov. 18, 1971 as Ser. No. 200,242 of Edward L. Morehouse, now U.S. Reissue Pat. No. 27,541. The copolymers of the latter patent contain from 40 to 200 dimethylsiloxy units as essentially the sole type of difunctional unit, and from 15 to 60 weight percent of the oxyalkylene content of the polyoxyalkylene blocks is constituted of oxyethylene. Also useful as stabilizers of flexible, polyether-based polyurethane foam including flame-retarded foam, are the block copolymers described in U.S. Pat. No. 3,657,305. The polysiloxane backbone of the organosilicones of the latter patent, contains an average of from 10 to 200 dimethylsiloxy units in combination with from 1 to 50 methyl-aralkylsiloxy units such as, in particular, methyl-phenylethylsiloxy units $[(CH_3)(C_6H_5CH_2CH_2)SiO]$. Other useful foam stabilizers for flexible polyetherbased foam are the block copolymers described in U.S. Pat. No. 3,686,254. Particularly useful stabilizers of flexible polyester-based polyurethane foam are the surfactants described in U.S. Pat. No. 3,594,334.

A second type of foam-stabilizing component which can be present in the formulations described herein are the branched block copolymers described in U.S. Pat. No. 2,834,748. Organosilicone foam stabilizers described in the latter patent include those containing a trifunctional siloxy unit to which three polyoxyalkylene blocks are bonded through dialkylsubstituted siloxy units. A preferred group are those having the formula, $MeSi[(OSiMe_2)_x(OC_aH_{2a})_vOX]_3$, wherein Me is methyl, $x$ has a value of at least one, $a$ is from 2 to 3, $v$ has a value of at least 5, and X is hydrogen or a monovalent hydrocarbyl group such as lower alkyl, butyl being especially suitable.

Particularly useful as foam-stabilizing components of flame-retarded flexible polyurethane formulations are the block copolymers wherein the polysiloxane blocks are trialkylsiloxy-endblocked and contain reoccurring difunctional dialkylsiloxy monomeric units in combination with reoccurring difunctional cyanoalkyl-alkylsiloxy or cyanoalkoxy-alkylsiloxy monomeric units, the mole ratio of the dialkylsiloxy units to the cyano-substituted siloxy units being about 10-200:3-100, and wherein the polysiloxane and polyoxyalkylene blocks are joined through an Si-C or an Si-O-C linkage, and from about 20 to about 65 weight percent of the oxyalkylene content of the polyoxyalkylene blocks is constituted of oxyethylene units. These block copolymers are described and claimed in copending application Ser. No. 279,883, filed Aug. 11, 1972, in the names of Bela Prokai and Bernard Kanner, now U.S. Pat. No. 3,846,462. A preferred class of such surfactants are the cyanopropyl-substituted block copolymers having the average forumla,

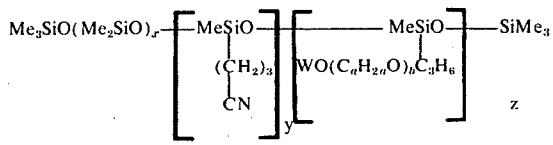

wherein: Me represents methyl; W represents a monovalent hydrocarbyl group (R'—), an acyl group [R'C(O)—] or a carbamyl group [R'NHC(O)—], wherein R' has from 1 to 12 carbon atoms; $x$ has an average value of from about 20 to about 100; $y$ has an average value of from about 4 to about 30; $z$ has an average value of from about 2 to about 10; $a$ has a value of from 2 to 4, provided from about 20 to about 65 weight percent of the oxyalkylene units of the polyoxyalkylene chain, $-(C_aH_{2a}O)_b-$, are constituted of oxyethylene; and $b$ has an average value such that the average molecular weight of the polyoxyalkylene chain is from about 1000 to about 6000.

Because of the high reactivity of high-resilience foam formulations, the foams are generally self-stabilizing and can be obtained without the use of stabilizing agents. However, it is usually desirable to include a silicone surfactant as an additional component of such formulations in order to minimize the tendency of the foam to settle and to control cell uniformity. Particularly effective for this purpose are the relatively low molecular weight polyoxyalkylene-polysiloxane block copolymers described and claimed in copending application Serial No. 84,181, filed October 26, 1970, of Edward L. Morehouse, now U.S. Pat. No. 3,741,917. Especially suitable as components of high-resilience formulations are the block copolymers described therein having the formula,

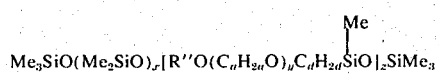

wherein: $x$ has an average value of from 2 to 7; $y$ has a value from 3 to 10; $z$ has an average value from 2 to 6; $a$ and $d$ each has a value from 2 to 4; and R'' is a monovalent hydrocarbon radical such as alkyl, aralkyl and aryl radicals, or an acyl group.

Also suitable as organosilicone components of high-resilience foam formulations are the relatively low molecular weight aralkyl-modified polymethylsiloxane oils described and claimed in copending application Ser. No. 305,713, filed Nov. 13, 1972, in the name of Edward L. Morehouse, and entitled, "Polyether Urethane Foam," now U.S. Pat. No. 3,839,384.

When used, the organosilicone component is usually present in high-resilience formulations in an amount between about 0.025 and about 2 parts by weight per 100 parts by weight of total polyol reactant.

Illustrative of suitable surfactant components of rigid foam formulations are copolymers wherein the polyoxyalkylene blocks are hydroxyl-terminated such as those described in U.S. Pat. No. 3,600,418.

The beta-amino carbonyl catalysts described herein are also effective catalytic components of flame-retarded foam formulations. The flame-retardants can be chemically combined in one or more of the other materials used (e.g., in the polyol or polyisocyanate), or they can be used as discrete chemical compounds added as such to the foam formulation. The organic flame-retardants preferably contain phosphorus or halogen, or both phosphorous and halogen. Usually, the halogen, when present, is chlorine and/or bromine. Flame-retardants of the discrete chemical variety include: 2,2-bis(bromomethyl)-1,3-propanediol (also known as dibromoneopentyl glycol); 2,3-dibromopropanol tetrabromophthalic anhydride; brominated phthalate ester diols such as those produced from tetrabromophthalic anhydride, propylene oxide and propylene glycol; tetrabromobisphenol-A; 2,4,6-tribromophenol; pentabromophenol; brominated anilines and dianilines; bis(2,3-dibromopropyl)ether of sorbitol; tetrachlorophthalic anhydride, chlorendic acid; chlorendic anhydride; diallyl chlorendate; chlorinated maleic anhydride; tris(2-chloroethyl)phosphate [(ClCH$_2$CH$_2$O)$_3$P(O)]; tris(2,3-dibromopropyl)phosphate; tris(1,3-dichloropropyl)phosphate; tris(1-bromo-3-chloroisopropyl)phosphate; tris(1,3-dichloroisopropyl)phosphate; bis(2,3-dibromopropyl) phosphoric acid or salts thereof; oxypropylated phosphoric and polyphosphoric acids; polyol phosphites such as tris(dipropylene glycol)phosphite; polyol phosphonates such as bis(dipropylene glycol)hydroxymethyl phosphonate; di-poly(oxyethylene)hydroxymethyl phosphonate; di-poly(oxypropylene)phenyl phosphonate; di-poly(oxypropylene)chloromethyl phosphonate; di-poly(oxypropylene)butyl phosphonate and O,O-diethyl-N,N-bis(2-hydroxyethyl)aminomethyl phosphonate. Also suitable are compounds having the formulas:

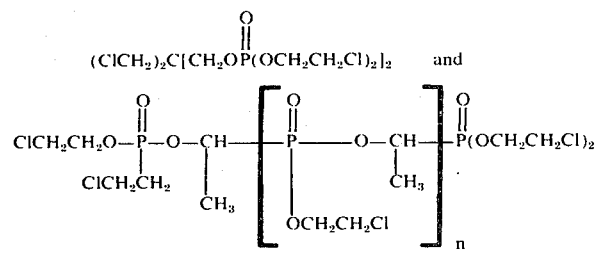

Other suitable flame-retardants comprise halogen-containing polymeric resins such as polyvinylchloride resins in combination with antimony trioxide and/or other inorganic metal oxides such as zinc oxide, as described in U.S. Pat. Nos. 3,075,927; 3,075,928; 3,222,305; and 3,574,149. It is to be understood that other flame-retardants known to the art may be used and that the aforesaid compounds may be employed individually or in combination with one another.

When used, the flame-retarding agent can be present in the foam formulations described herein in an amount from about 1 to about 30 parts by weight per 100 parts by weight of the polyol reactant, the particular amount employed depending largely on the efficiency of any given agent in reducing flammability.

If desired, other additional ingredients can be employed in minor amounts in producing the polyurethane foams in accordance with the process of this invention. Illustrative of such additives that can be employed are: the aforementioned cross-linking agents such as glycerol, diethanolamine, triethanolamine and their oxyalkylene adducts; additives to enhance load-bearing properties such as methylene-di-ortho-chloroaniline (MOCA); as well as fillers, dyes, pigments, anti-yellowing agents and the like.

The cellular urethane polymers of the invention may be formed in accordance with any of the processing techniques known to the polyurethane art such as the "one-shot", quasi-prepolymer and prepolymer techniques. For example, in accordance with the "one-shot" process, foamed products are produced by carrying out the reaction of the polyisocyanate and the polyol reactants in the presence of the beta-amino carbonyl-containing catalyst systems described herein, simultaneously with the foaming operation. This one-step process usually employed in producing flexible foam including high-resilience foam, although it is also applicable to rigids. In preparing foamed products in accordance with the quasi-prepolymer technique, the polyisocyanate is first reacted with a portion of the polyol reactant to give a product having a high percentage of free —NCO groups (e.g., from 20 to 50 percent), and the product is subsequently foamed by reaction with additional polyol and foaming agent in the presence of the beta-amino carbonyl catalysts. In the prepolymer technique, the polyisocyanate is reacted with a slightly less than stoichiometric quantity of the polyol reactant to form a prepolymer having a low percentage (e.g., from 1 to 10 percent) of free —NCO groups, followed by reaction of the prepolymer with a blowing agent such as water in the presence of the catalyst systems described herein to form the cellular material. These various multi-stage methods are more usually applied to rigid formulations.

In general, final or post-curing of the foam products is achieved by allowing the foam to stand at ambient temperatures until a tack-free product is obtained, or by subjecting the foam to elevated temperatures up to about 500°F. in order to achieve more rapid curing. In view of the higher reactivity of the combination of reactants employed in producing high-resilience foams, however, a sufficiently high degree of curing is achieved during foam formation without the necessity of subjecting the foam to conventional high temperature (e.g., 300°–500°F.) post-curing procedures which are otherwise applied in the commercial manufacture of flexible foams from less highly reactive flexible foam formulations.

In the specific application of the beta-amino amides and beta-amino esters described herein as catalytic components of molded, high-resilience foam formulations, the mold is charged with the foamable reaction mixture either at ambient temperature or pre-heated to a temperature of from about 70°F. to about 200°F., in an amount sufficient to at least completely fill the mold. The mold is then closed and the reaction mixture is allowed to foam and cure itself. In view of the excellent mold-release characteristics of the high-resilience foams produced in accordance with the present invention, the foamed product is readily removed from the mold without substantial damage to the foam surface. The demolded foam is suitable for end-use application without further curing. It is to be understood, however, that such foam may be subjected to further curing, as desired.

The end-use applications of cellular polyurethanes are well known. Thus, the polyurethane foams produced in accordance with the present invention are useful as textile interliners, cushioning material, mattresses, paddings, carpet underlay, packaging, gaskets, sealers, thermal insulators and the like.

The following examples are offered as further illustrative of the present invention and are not to be construed as unduly limiting.

Examples 1–10 describe the preparation of illustrative beta-amino carbonyl catalysts, designated herein as Amine Catalysts I-X, respectively, which were employed as catalyst components in the polyurethane foam preparations of the remaining examples. Of these, Amine Catalysts IV, V, VI and VII are novel compounds. In Examples 1–10, the Amine reactant was substantially anhydrous and the reaction media contained less than about 5 weight percent water, expressed on the basis of amine reactant. The yields of product are based on the number of moles of reactant present in the limiting amount.

ucts, Amine Catalysts I, II and III are known compounds and were produced in a purity of about 75–98 percent, as indicated by gas chromatographic analysis. Amine Catalyst IV is a novel compound and its structure was verified by infrared and nuclear magnetic resonance spectroscopy.

TABLE I

| Example No. | No. | Beta-Amino Amide Catalyst Structure | Reactant A (grams) | Reactant B (grams) |
|---|---|---|---|---|
| 1 | I | 3-dimethylamino-N,N-dimethylpropionamide $(CH_3)_2N-CH_2CH_2C(O)N(CH_3)_2$ | Dimethylamine (419) | Ethyl acrylate (300) |
| 2 | II | 3-dimethylamino-2-methyl-N,N-dimethylpropionamide $(CH_3)_2N-CH_2CHC(O)N(CH_3)_2$ $\quad\quad\quad\quad\quad\quad CH_3$ | Dimethylamine (135) | Methyl methacrylate (100) |
| 3 | III | 3-diethylamino-N,N-diethylpropionamide $(C_2H_5)_2N-CH_2CH_2C(O)N(C_2H_5)_2$ | Diethylamine (219) | Methyl acrylate (86.1) |
| 4 | IV | 3-dimethylamino-N,N-dimethylbutyramide $(CH_3)_2NCHCH_2C(O)N(CH_3)_2$ $\quad\quad\quad CH_3$ | Dimethylamine (117) | Methyl crotonate (81) |

| Example No. | Temperature (°C.) | Pressure (p.s.i.g.) | Time (hours) | Product Recovery °C. | mm.Hg | Yield % |
|---|---|---|---|---|---|---|
| 1 | 180–200 | 200–400 | 20 | 103–105 | 10 | 95 |
| 2 | 190–200 | 400–500 | 20 | 61–62 | 3 | 44 |
| 3 | 180–200 | 200–320 | 32 | 90–91 | 3 | 22 |
| 4 | 185–205 | 250–350 | 32 | 74–79 | 2 | 34 |

EXAMPLES 1–4

In accordance with these examples beta-dialkylamino-N,N-dialkylamides, designated herein as Amine Catalysts I-IV, respectively, were prepared by the reaction of secondary amines (Reactant A) and alkyl esters of alpha,beta-unsaturated carboxylic acids (Reactant B) in the presence of phenothiazine (0.7 gram) and p-methoxyphenol (0.7 gram) as inhibitors, under elevated temperature and pressure conditions in a stainless steel rocker bomb. The particular reactants, relative proportions thereof and reaction conditions of temperature, pressure and time are given in Table I. After the indicated reaction time, the reactors were cooled and the respective reaction mixtures were transferred to a still except that, in Example 1, the reaction mixture was partially stripped of volatiles after discharge from the pressure reactor and a portion (200 grams) of the partially stripped material was combined with phenothiazine (1.0 gram), p-methoxyphenol (0.5 gram) and Humble 1243 oil as a pot-boiler (20 grams). In each example, the respective products were recovered by distillation under the temperature and reduced pressure conditions specified in Table I. Of these prod-

EXAMPLE 5

Preparation of 3-Diethylamino-N,N-Dimethylpropionamide

In accordance with this example, anhydrous diethylamine (44 grams) and N,N-dimethylacrylamide (60 grams) were heated at reflux temperature (about 56°–60°C.) for 48 hours. After this period of time, the reaction mixture was subjected to distillation to separate unreacted amine and amide followed by recovery of product in 86 percent yield at 70°C. and 2 mm. mercury pressure. The liquid product (purity = about 95 percent is designated herein as Amine Catalyst V, and has the formula, $(C_2H_5)_2N\text{-}CH_2CH_2C(O)N(CH_3)_2$. The structure of this novel product was confirmed by infrared functional analysis and purity by gas-liquid chromatographic analysis.

EXAMPLE 6

Preparation of 3-(N-Morpholino)-N',N'-Dimethylpropionamide

Morpholine (45 grams) was added dropwise to a stirred reaction flask containing N,N-dimethylacrylamide (50 grams). After the addition was completed, the reaction mixture was stirred for 24 hours at 30°–70°C. After this period of time, the reaction mixture was heated at 110°C. and 10 mm. mercury pressure to remove unreacted starting materials. The remaining material was a viscous liquid and was recovered in a 95 percent yield. This residue product contains about 98 weight per cent of the novel compound,

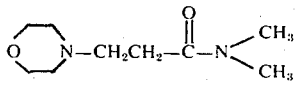

and is designated herein as Amine Catalyst VI. A sample of this material was distilled at 114°–115°C. and 1 mm. mercury pressure without appreciable decomposition. The structure was verified by infrared and nuclear magnetic resonance spectroscopy.

EXAMPLE 7

Preparation of
N,N'-Piperazino-bis[3-(N'',N''-dimethylpropionamide)]

To a stirred solution of piperazine (25.0 grams) dissolved in ethanol (30 grams), N,N-dimethylacrylamide (59.4 grams) was added. After the addition, the reaction mixture was stirred at 30°–40°C. for 2 hours. The precipitated material was filtered, washed with ethanol and dried under vacuum. The solid product (76 percent yield) has a melting point of 137°–138°C. and the structure:

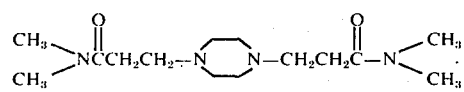

as determined by infrared and nuclear magnetic resonance spectroscopy and elemental analysis. Anal. Calcd. for $C_{14}H_{28}N_4O_2$: C, 59.1; H, 9.9; N, 19.7. Found: C, 58.0 and 58.4; H, 9.59 and 9.52; N, 19.5 and 19.4. This novel product is designated herein as Amine Catalyst VII.

EXAMPLE 8

Preparation of Ethyl
3-(N,N-Dimethylamino)propionate

To a chilled (−15°C.) reaction vessel there was added: anhydrous dimethylamine (100 grams); ethyl acrylate (250 grams); phenothiazine (0.5 gram); and p-methoxyphenol (0.5 gram). The mixture was maintained at −13°C. for 2 hours with stirring after which the temperature was allowed to rise to about 25°C. Unreacted dimethylamine and ethyl acrylate were removed by distillation. The product was recovered by distillation at 58°C. and 10 mm. mercury pressure in a yield of 97 percent. The product, designated herein as Amine Catalyst VIII, has the formula, $(CH_3)_2NCH_2CH_2C(O)OC_2H_5$, as verified analytically by infrared spectroscopy.

EXAMPLE 9

Preparation of Ethyl 3-(N,N-Diethylamino)propionate

The following materials were charged to the reaction vessel: anhydrous diethylamine (292 grams); ethyl acrylate (200 grams); phenothiazine (1.0 gram); and p-methoxyphenol (1.0 gram). This mixture was heated at reflux (about 56°–60°C.) for 24 hours. At the end of this period, unreacted amine was removed by distillation. The product was recovered at 80°–81°C. and 10 mm. mercury pressure in a yield of 96 percent. The product is designated herein as Amine Catalyst IX and has the formula, $(C_2H_5)_2N-CH_2CH_2-C(O)OC_2H_5$, as verified analytically by infrared spectroscopy.

EXAMPLE 10

Preparation of 2-(N,N-dimethylamino)ethyl
3-(N',N'-dimethylamino)propionate

Anhydrous dimethylamine (19.8 grams) was added dropwise to 2-(N,N-dimethylamino)ethyl acrylate (31.5 grams) in a magnetically-stirred, ice-cooled reaction vessel at such a rate that the temperature did not exceed 40°C. The addition of dimethylamine was complete in about 10 minutes. After allowing the reaction mixture to stir overnight at room temperature, it was subjected to reduced pressure (about 20 mm. Hg) to remove unreacted dimethylamine. Gas-liquid chromatographic analysis indicated that the residue product was 96.5 percent pure. The structure of the product,

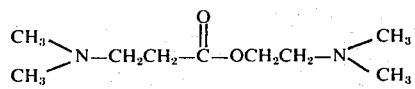

was verified spectroscopically (nuclear magnetic resonance and infrared) and by elemental analysis. Anal. Calc'd. for $C_9H_{20}N_2O_2$: C, 57.4; H, 10.6; N, 14.9. Found: C, 57.3; H, 10.5; N, 14.8. This product is designated herein as Amine Catalyst X.

In the examples which follow, molded and free-rise cellular polyurethanes were prepared employing the above-described Amine Catalysts I-X as catalyst components of a variety of foam formulations. In some examples, these beta-amino amide and ester catalysts were used as the sole tertiary amine catalytic component of the reaction mixtures whereas in other instances they were used as components of mixed catalyst systems. In preparing the molded foams of Examples 11–16, the procedure employed was that described below as Foam Procedure I. The manipulative steps involved in the preparation of the free-rise foams of Examples 17–46 were as described under Foam Procedure II.

FOAM PROCEDURE I

An aluminum mold (4 inches or 2 ½ inches × 15 inches × 15 inches) is prepared by first waxing lightly with Brulin Permamold Release Agent and then preheating in a 140°C. oven for about 10 minutes to raise the temperature of the mold to 175°–200°F. Excess mold-release agent is wiped off and the mold is allowed to cool to 120°F. before foaming. The initial mixing of the components of the foam formulation is started when the mold is cooled to about 130°F. The purpose of pre-heating the mold to the initial high temperature is to remove solvent from the mold-release agent. All components of the reaction mixture, except the polyisocyanate reactant, are measured or weighted into a one-half gallon, 5 inch diameter, cylindrical, cardboard carton and mixed 60 seconds with a 2 ½ inch, 6-blade turbine at 4000 revolutions per minute. The polyisocyanate reactant is then weighed into the mixture of other components, stainless-steel baffles designed for the ½ gallon carton are inserted, and mixing is continued for 5 seconds. The carton is then lowered to allow the mixer to drain, and the contents are quickly poured into the mold. The mold lid is closed and clamps are placed around the mold to permit flashout. "Exit time" is observed and defined as the time when all four top holes of the mold are full, that is, when the foam begins to exude from all four holes of the mold. "Pop time" is observed and defined as the time when extruded parts stop bubbling. The 4 inches mold is demolded after standing at room temperature for 10 minutes whereas the 2 ½ inches mold is demolded after 8 minutes. After trimming around the edges with scissors, the foam sample is weighted before running through rollers four times to crush cells open, and is then allowed to cure for three days at room temperature before being submitted for physical property measurements.

FOAM PROCEDURE II

The polyol and polyisocyanate reactants and surfactant (and, when employed, the flame-retardant and cross-linking agents) are weighed into a ½-gallon, 5-inch diameter, cylindrical cardboard carton. The water and catalytic amine components are measured and blended together in a small beaker. The tin catalyst is measured into a hypodermic syringe. Eleven stainless-steel baffles are inserted into the carton and centered on a drill press equipped with a 1.65-inch, 4-blade turbine. A timer is pre-set for a total of 90 seconds. The mixer is started at 2400 revolutions per minute and continued for 60 seconds, except that in those formulations containing polymer/polyols, the mixer is started at 3000 revolutions per minute. The mixer is stopped manually for a 15-second de-gassing period. At 75 seconds on the timer, mixing is continued for 5 seconds before adding the aqueous amine premix. Mixing is continued 5 seconds and the tin catalyst is added after an additional 5 seconds of mixing. The blended contents are poured into a 14 inch × 14 inch × 6 inch cardboard box. Both the "cream time" and "rise time" are recorded which terms denote the interval of time from the formation of the complete foam formulation to: (1) the appearance of a creamy color in the formulation, and (2) the attainment of the maximum height of the foam, respectively. The foam is allowed to stand at room temperature for about one day before being submitted for physical property measurements.

The physical properties which were determined for the flexible foams produced in the examples and control runs were measured in accordance with the standardized test procedures given below.

Porosity (Air), which is a comparative measurement of the degree of openness of the cells of flexible foams, was determined in accordance with the following test procedure: The test specimen of foam (4 inches × 4 inches × ½ inch) is compressed between two pieces of flanges plastic tubing (2 ¼ inches I.D.) of an air porosity assembly maintained under an air pressure of 14.7 pounds. Air is drawn through the thickness (½ inch) of the foam specimen at a velocity controlled to maintain a differential pressure of 0.1 inch of water across the thickness dimension. The air flow necessary to develop the requisite pressure differential is recorded and the air flow per unit area of the foam specimen is reported as the porosity of the foam.

Resiliency of both the molded and free-rise foams was determined in accordance with ASTM D-1564-69.

Density, Tensile Strength, Elongation, Tear Resistance and Compression Set were measured as described under (1) ASTM D-2406-68 for the molded foams produced in accordance with Foam Procedure I, and (2) ASTM D-1564-69 for the free-rise foams produced in accordance with Foam Procedure II.

Indentation Load Deflection (ILD Values) to 25% and 65% deflections were measured in accordance with (1) ASTM D-2406-68 for the molded foam samples, the thickness of the sample being 2 ½ inches or 4 inches depending upon whether the 2 ½ inches or 4 inches mold was used, and (2) ASTM D-1564-69 for the free-rise foams, the test sample being cut to a 4 inch thickness. Return Value is the percentage ratio of the load required to support the return 25% indentation after one minute as compared to the load required to support the initial 25% indentation after one minute. Load Ratio is the ratio of the 65% and 25% ILD values, respectively.

The following Examples 11–16 demonstrate the efficacy and advantages of beta-amino amide and ester catalysts described herein when employed as direct replacements for N-ethylmorpholine in high-resilience foam formulations.

EXAMPLES 11 and 12

Molded foams were prepared employing 3-dimethylamino-N,N-dimethylpropionamide (Amine Catalyst I) in Example 11, 2-(N,N-dimethylamino)ethyl 3-dimethylaminopropionate (Amino Catalyst X) in Example 12, and N-ethylmorpholine in Control Run K-1, as catalyst components of a high-resilience foam formulation, designated herein as Foam Formulation A. The composition of this reaction mixture as employed in Examples 11 and 12 and Control Run K-1 is given in Table II which follows.

TABLE II - FOAM FORMULATION A

| Component | Parts By Weight Control K-1 | Examples 11 and 12 |
|---|---|---|
| Polyol A: An ethylene oxide-capped, glycerol-started poly(oxypropylene) triol having a Hydroxyl No. of about 34, a molecular weight of about 5000, and a primary hydroxyl content of 70–75 mole per cent. | 60 | 60 |
| Polyol B: A polymer/polyether polyol having a Hydroxyl No. of about 28 and based on (parts by weight): styrene (10), acrylonitrile (10) and Polyol A (80), produced by polymerizing said monomers in Polyol A. | 40 | 40 |
| Polyisocyanate A: A mixture of: (1) 80 weight per cent of the 2,4- and 2,6- isomers of tolylene diisocyanate, the weight ratio of said isomers being 80:20, respectively; and (2) 20 weight per cent of a polyphenylmethylene polyisocyanate having an average -NCO functionality of 2.7 and a free -NCO content of 30.5–32.3 weight per cent. | 36.45 | 36.45 |
| Water | 3.0 | 3.0 |

TABLE II - FOAM FORMULATION A-continued

| Component | Parts By Weight Control K-1 | Parts By Weight Examples 11 and 12 |
|---|---|---|
| Amine Catalysts | | |
| Amine Catalyst A: A 70 weight per cent solution of bis[2-(N,N-dimethylamino)ethyl]ether in dipropylene glycol. | 0.08 | 0.08 |
| Amine Catalyst B: A 33 weight per cent solution of triethylenediamine in dipropylene glycol. | 0.25 | 0.25 |
| N-Ethylmorpholine | 0.80 | None |
| Amine Catalysts I and X, respectively. | None | 0.20 |
| Dibutyltin dilaurate | 0.03 | 0.03 |
| Surfactant A /1/ | 0.07 | — |
| Surfactant B /2/ | — | 0.05 |

/1/ A phenylethyl-modified polymethylsiloxane oil having the average composition, $Me_3SiO(Me_2Si-O)_x[(C_6H_5C_2H_4)(Me)SiO]_ySiMe_3$ wherein Me represents methyl and the average values of x and y are 3.0 and 1.5, respectively.
/2/ Same as Surfactant A, except average values of x and y are 3.8 and 1.9, respectively.

The foams of Exampes 11 and 12, designated for convenience as Foam Nos. 1 and 2, respectively as well as Control Foam K-1, were prepared following Foam Procedure I, employing the 4 inches × 15 inches × 15 inches aluminum mold heated to 120°F. Upon completion of foam formation, Control Foam K-1 was easily removed from the mold after 10 minutes residence time and foam surface and freedom from tendency to shrink were excellent. However, the odor level emanating from the freshly demolded foam was very high and, although diminishing in intensity with time, this odor persisted for several hours. With respect to Foam No. 1, demoled characteristics were also excellent and the cellular structure was fine (as opposed to coarse). In the case of Foam No. 2, demold characteristics were good and, although the foam surface structure was not as good as that of Control Foam K-1 or Foam No. 1, it was satisfactory. With respect to both Foam Nos. 1 and 2, the odor level emanating from the freshly demolded foam was very low and clearly in improvement over the control foam. These and other results as well as physical property data of the respective foams are given in Table III.

TABLE III - HIGH-RESILIENCE FOAM (Molded)

| Example No. | — | 11 | 12 |
|---|---|---|---|
| Control Run | K-1 | — | — |
| Foam No. | K-1 | 1 | 2 |
| Foam Formulation A | | | |
| N-Ethylmorpholine, p.p.h.p. | 0.80 | None | None |
| Amine Catalyst I /1/, p.p.h.p. | None | 0.20 | — |
| Amine Catalyst X /2/, p.p.h.p. | None | — | 0.20 |
| Exit Time, seconds | 61 | 53 | 59 |
| Pop Time, seconds | 121 | 100 | 110 |
| Hot Foam Odor | High | Low | Low |
| Foam Properties | | | |
| Basal cell structure | Good | Good | Fair |
| Resilience, % ball rebound | 63 | 64 | 64 |
| Porosity, ft.³/min./ft.² | 61 | 53.1 | 50.6 |
| Density, lbs./ft.³ | 1.96 | 1.90 | 1.93 |
| ILD (4"), lbs./50 in.² | | | |
| 25% deflection | 22.3 | 20.3 | 24.2 |
| 65% deflection | 62.0 | 56.0 | 63.0 |
| 25% return | 17.3 | 16.0 | 19.0 |
| Return value, % | 77.6 | 78.8 | 78.5 |
| Load Ratio | 2.78 | 2.76 | 2.62 |
| Compression Sets, % | | | |
| 75% | 13.0 | 12.6 | 13.0 |
| 50% After Humid Aging /3/ | 26.5 | 24.9 | 24.2 |
| Tensile strength, p.s.i. | 24.0 | 22.6 | 21.8 |
| Elongation, % | 199 | 204 | 192 |
| Tear Resistance, lbs./in. | 2.41 | 2.22 | 2.17 |
| Humid Age Load Loss, % /3/ | 22.4 | 20.6 | 20.2 |

/1/ 3-Dimethylamino-N,N-dimethylpropionamide.
/2/ 2-(N,N-Dimethylamino)ethyl 3-Dimethylaminopropionate.
/3/ Five hours at 120°C. in 100% relative humidity.

The results of Table III show that the improvement of low residual foam odor afforded by the catalysts of this invention is achieved without sacrifice of the good overall combination of physical properties possessed by the control foam. Further, as evinced by the interval of time required for the foam to exude from the mold, the reactivity of the respective reaction mixtures containing Amine Catalysts I and X was excellent even though the concentration of these catalysts was only one-fourth the concentration (on a weight basis) of N-ethymorpholine. In fact, as reflected by comparison of the respective exit times, the reactivity of the formulation containing 3-dimethylamino-N,N-dimethylpropionamide (Example 11) in an amount of 0.20 part per 100 parts of total polyol (p.p.h.p.), was 12–14 per cent higher than that of the control formulation containing 0.80 p.p.h.p. of N-ethylmorpholine.

EXAMPLES 13–16

In accordance with these examples, molded foams were prepared employing Amine Catalysts II-V, respectively, as direct replacements for N-ethylmorpholine (COntrol Run K-2) in a high-resilience foam formulation, designated herein as Foam Formulation B. The composition of this reaction mixture is given in the following Table IV.

TABLE IV - FOAM FORMULATION B

| Component | Parts By Weight Control K-2 | Parts By Weight Examples 13-16 |
|---|---|---|
| Polyol A/1/ | 60 | 60 |
| Polyol B/1/ | 40 | 40 |
| Polyisocyanate A/1/ | 34.38 | 34.38 |
| Water | 2.80 | 2.80 |
| Amine Catalysts | | |
| Amine Catalyst A/1/ | 0.08 | 0.08 |
| Amine Catalyst B/1/ | 0.30 | 0.30 |
| N-Ethylmorpholine | 0.80 | None |
| Amine Catalysts II-V, respectively. | None | 0.15 |
| Dibutyltin dilaurate | 0.03 | 0.03 |
| Surfactant C/2/ | 1.50 | 1.00 |

/1/ Same as in Foam Formulation A of Table II.
/2/ A polysiloxane oil having the average composition, $Me_3SiO(Me_2SiO)_4[MeO(C_2H_4O)_3C_2H_4SiMeO]_{2.x}SiMe_3$ where Me is methyl, employed as a 10 weight per cent solution in Polyol A.

The foams of Examples 13–16, designated for convenience as Foam Nos. 3–6, respectively, as well as Control Foam K-2 were prepared following Foam Procedure I, employing the 2 ½ inches × 15 inches × 15 inches aluminum mold heated to 120°F. Upon completion of foaming, it was found that in each instance demold characteristics were excellent as reflected by lack of foam tenderness and ease of demolding. The surface structure of Control Foam K-2 and Foam Nos. 3–6 was also good. However, the odor level emanating from the freshly demolded control foam was high. With respect to Foam Nos. 3–6, on the other hand, hot foam odor was low and clearly an improvement over that of the control foam. Other results and foam physical property data are given in Table V.

TABLE V

| | High-Resilience Foam (Molded) | | | | |
|---|---|---|---|---|---|
| Example No. | — | 13 | 14 | 15 | 16 |
| Control Run No. | K-2 | — | — | — | — |
| Foam No. | K-2 | 3 | 4 | 5 | 6 |
| Foam Formulation B | | | | | |
| N-Ethylmorpholine, p.p.h.p. | 0.80 | None | None | None | None |
| Amine Catalyst II /1/, p.p.h.p. | None | 0.15 | — | — | — |
| Amine Catalyst III /2/, p.p.h.p. | None | — | 0.15 | — | — |
| Amine Catalyst IV /3/, p.p.h.p. | None | — | — | 0.15 | — |
| Amine Catalyst V /4/, p.p.h.p. | None | — | — | — | 0.15 |
| Exit Time, seconds | 45 | 47 | 48 | 46 | 49 |
| Pop Time, seconds | 107 | 114 | 125 | 112 | 109 |
| Hot Foam Odor | High | Low | Low | Low | Low |
| Foam Properties | | | | | |
| Basal cell structure | Good | Good | Good | Good | Good |
| Resiliency, % ball rebound | 60 | 63 | 61 | 64 | 63 |
| Porosity, ft.$^3$/min./ft.$^2$ | 21.5 | 39.5 | 26.5 | 32.0 | 21.5 |
| Density, lbs./ft.$^3$ | 2.69 | 2.64 | 2.65 | 2.72 | 2.77 |
| ILD (2½″), lbs./50 in.$^2$ | | | | | |
| 25% deflection | 35.5 | 36.0 | 34.9 | 35.4 | 35.0 |
| 65% deflection | 93.2 | 95.7 | 92.3 | 94.9 | 92.6 |
| 25% return | 28.6 | 29.0 | 28.2 | 28.6 | 28.1 |
| Return value, % | 80.6 | 80.5 | 80.8 | 80.8 | 80.3 |
| Load Ratio | 2.63 | 2.66 | 2.65 | 2.68 | 2.65 |
| Compression Sets, % | | | | | |
| 75% | 11.1 | 10.4 | 10.4 | 11.1 | 11.4 |
| 50% After Humid Aging /5/ | 21.5 | 20.6 | 19.1 | 21.0 | 21.6 |
| Tensile strength, p.s.i. | 26.5 | 26.5 | 28.2 | 29.0 | 26.2 |
| Elongation, % | 172 | 177 | 193 | 186 | 176 |
| Tear Resistance, lbs./in. | 2.34 | 2.38 | 2.46 | 2.38 | 2.44 |
| Humid Age Load Loss, %/5/ | 30.7 | 26.9 | 26.5 | 23.9 | 24.8 |

/1/ 3-Dimethylamino-2-methyl-N,N-dimethylpropionamide.
/2/ 3-Diethylamino-N,N-diethylpropionamide.
/3/ 3-Dimethylamino-N,N-dimethylbutyramide.
/4/ 3-Diethylamino-N,N-dimethylpropionamide.
/5/ Five hours at 120°C. in 100% relative humidity.

The results of Table V show that the improvement is hot foam odor realized by use of Amine Catalysts II-V in place of N-ethylmorpholine was achieved without impairment of the overall combination of physical properties possessed by the control foam. Thus, the resiliency and porosity of Foam Nos. 3–6, were at least as good as that of the control foam and their load-bearing, compression set and other properties were also good. In addition to the improvement in hot foam odor, the humid age load loss of Foam Nos. 3–6 was at least 12 percent less than and thus superior to that of the control foam.

EXAMPLE 17

In accordance with this example, 3-dimethylamino-N,N-dimethylpropionamide (Amine Catalyst I) was employed in combination with bis[2-(N,N-dimethylamino)ethyl]ether as the amine catalysts of a free-rise, high-resilience foam formulation containing tris(2,3-dibromopropyl)phosphate as an added flame-retarding agent. A control foam was also prepared (Control Run K-3) employing the same formulation except that a 33 weight percent solution of triethylenediamine was employed as the sole amine catalyst. The composition of the respective reaction mixtures (Foam Formulation C) is given in Table VI. The foam of this example and the control foam were prepared following freerise Foam Procedure II. The results and foam physical property data are also given in Table VI.

TABLE VI

| HIGH-RESILIENCE FOAM (Free-Rise) | | |
|---|---|---|
| Example No. | — | 17 |
| Control Run No. | K-3 | — |
| Foam No. | K-3 | 7 |
| Foam Formulation C, Parts by Weight | | |
| Polyol B /1/ | 50 | 50 |
| Polyol C: An ethylene oxide-capped, glycerol started poly(oxypropylene) triol having a Hydroxyl No. of about 27, a molecular weight of about 6000, and a primary hydroxyl content of 80–85 mole per cent. | 50 | 50 |
| Polyisocyanate B: A mixture of the 2,4- and 2,6-isomers of tolylene diisocyanate, the weight ratio of said isomers being 80:20, respectively. (Index = 110) | 28.3 | 28.3 |
| Diethanolamine | 0.8 | 0.8 |
| Water | 2.0 | 2.0 |
| Amine Catalysts | | |
| Amine Catalyst B: A 33 weight per cent solution of triethylenediamine in dipropylene glycol. | 0.40 | None |
| Bis[2-(N,N-dimethylamino)ethyl]ether (undiluted) | None | 0.06 |
| Amine Catalyst I /2/ | None | 0.24 |
| Stannous octoate | 0.06 | 0.06 |
| Tris(2,3-dibromopropyl)phosphate | 2.0 | 2.0 |
| Surfactant C /3/ | 1.0 | 1.0 |
| Cream Time, seconds | 6 | 6 |
| Rise Time, seconds | 155 | 185 |
| Foam Properties | | |
| Resiliency, % ball rebound | 62 | 61 |
| Porosity, ft.$^3$/min./ft.$^2$ | 37 | 40 |
| Density, lbs./ft.$^3$ | 2.98 | 2.96 |
| ILD (4″), lbs./50 in.$^2$ | | |
| 25% deflection | 35.2 | 34.3 |
| 65% deflection | 79.3 | 77.2 |
| 25% return | 28.8 | 27.0 |
| Return value, % | 81.8 | 78.8 |
| Load Ratio | 2.25 | 2.25 |
| Compression Sets, % | | |
| 75% | 5.7 | 6.1 |
| 50% | 7.2 | 7.5 |
| Tensile strength, p.s.i. | 21.1 | 20.6 |
| Elongation, % | 187 | 177 |
| Tear Resistance, lbs./in. | 2.71 | 3.05 |
| Humid Age Load Loss, % /4/ | 35.6 | 34.5 |
| 50% Compression Set After Humid Aging, % /4/ | 11.9 | 13.4 |

/1/ As defined in Table II.
/2/ 3-Dimethylamino-N,N-dimethylpropionamide.
/3/ As identified in Table IV.
/4/ Aged five hours at 120°C. in 100% relative humidity.

The results of Table VI indicate that Foam No. 7 and Control Foam K-3 had excellent resiliency and about the same overall combination of physical properties. Both foams were also of fine cell structure. Although formulation reactivity, as reflected by rise time, was higher in the case of the control reaction mixture, reactivity of the reaction mixture employed in Example 17 was good. The higher reactivity observed for triethylenediamine is offset by a number of advantages offered by use of 3-dimethylamino-N,N-dimethyl-propionamide in combination with bis[2-(N,N-dimethylamino)-ethyl]ether. One such advantage is that the latter catalysts are both normally liquid materials whereas triethylenediamine, although an excellent catalyst, has the processing disadvantage of being a solid. Perhaps more significantly, triethylenediamine is also associated with a relatively strong amine odor which was noticeable as a residual odor in the freshly prepared control foam. On the other hand, freshly prepared Foam No. 7 was completely free of any amine odor.

EXAMPLES 18 and 19

In accordance with these examples, 3-(N-morpholino)-N',N'-dimethylpropionamide and N,N'-piperazino-bis[3-(N'',N''-dimethylpropionamide)], designated herein as Amine Catalysts VI and VII, were employed as the respective sole amine catalysts of a reaction mixture (Foam Formulation D) which otherwise contains components employed commercially for the manufacture of free-rise (slabstock) flexible polyurethane foam. The foams were prepared following Foam Procedure II. The composition of Foam Formulation D and the results are given in Table VII which follows.

TABLE VII

| Example No. | 18 | 19 |
|---|---|---|
| Foam No. | 8 | 9 |
| Foam Formulation D, Parts By Weight | | |
| Polyol D: A glycerol-started poly(oxypropylene) triol having a Hydroxyl No. of about 56. | 100 | 100 |
| Polyisocyanate B: A mixture of the 2,4- and 2,6- isomers of tolylene diisocyanate present in a weight ratio of 80:20, respectively. (Index = 105) | 49.75 | 49.75 |
| Water | 4 | 4 |
| Stannous octoate | 0.275 | 0.30 |
| Surfactant D /1/ | 1.0 | 1.0 |
| Amine Catalysts: | | |
| Amine Catalyst VI /2/ | 0.40 | — |
| Amine Catalyst VII /3/ | — | 0.40 |
| Cream Time, seconds | 13 | 13 |
| Rise Time, seconds | 111 | 110 |
| Foam Properties | | |
| Resiliency, % ball rebound | 41 | 42 |
| Porosity, ft.$^3$/min./ft.$^2$ | 84 | 65.5 |
| Density, lbs./ft.$^3$ | 1.79 | 1.71 |
| ILD (4''), lbs./50 in.$^2$ | | |
| 25% deflection | 37.0 | 38.0 |
| 65% deflection | 80.0 | 73.5 |
| 25% return | 25.4 | 23.9 |
| Return value, % | 68.7 | 62.9 |
| Load Ratio | 2.16 | 1.94 |
| Compression Sets, % | | |
| 90% | 5.11 | 5.28 |
| 50% After Humid Aging /4/ | 7.17 | 7.6 |
| Tensile strength, p.s.i. | 16.7 | 15.2 |
| Elongation, % | 217 | 202 |
| Tear Resistance, lbs./in. | 2.47 | 2.34 |
| Humid Age Load Loss, % /4/ | 15.4 | 12.9 |

/1/ A polyoxyalkylene-polysiloxane block copolymer having the average composition: MeSi[(OSiMe$_2$)$_{n-4}$ (OC$_3$H$_4$)$_{18}$(OC$_3$H$_6$)$_{13}$OC$_4$H$_9$]$_3$ wherein Me is methyl.
/2/ 3-(N-Morpholino)-N',N'-dimethylpropionamide.
/3/ N,N'-Piperazino-bis[3-(N'',N''-dimethylpropionamide)].
/4/ Five hours at 120°C. in 100% relative humidity.

The data of Table VII demonstrate that Amine Catalysts VI and VII are catalytically active in promoting the isocyanate-water reaction, as reflected by rise time and the highly porous nature of the foam products. The data also indicated the efficacy of these catalysts in allowing for the formation of flexible foams having a good combination of physical properties including low compression set valves and low load losses after humid aging. These foams were also completly odorless.

EXAMPLES 20–23

In accordance with these examples, 3-dimethylamino-N,N-dimethylpropionamide (Amine Catalyst I) and 2-(N,N-dimethylamino)ethyl 3-dimethylaminopropionate (Amine Catalyst X) were employed as the respective sole amine catalysts of Foam Formulation D (Table VII) in place of Amine Catalysts VI and VII. The foams were prepared following free-rise Foam Procedure II. The concentration of amine catalyst and stannous octoate employed in these examples and the results are given in Table VIII which follows.

TABLE VIII

| FLEXIBLE FOAMS (Free-Rise) | | | | |
|---|---|---|---|---|
| Example No. | 20 | 21 | 22 | 23 |
| Foam No. | 10 | 11 | 12 | 13 |
| Foam Formulation D /1/ | | | | |
| Stannous octoate, p.p.h.p. | 0.3 | 0.425 | 0.25 | 0.275 |
| Amine Catalyst I /2/, p.p.h.p. | 0.1 | 0.20 | — | — |
| Amine Catalyst X /3/, p.p.h.p. | — | — | 0.40 | 0.20 |
| Cream Time, seconds | 11 | 11 | 12 | 13 |
| Rise Time, seconds | 90 | 70 | 100 | 103 |
| Foam Properties | | | | |
| Resiliency, % ball rebound | 45 | 44 | 45 | 46 |
| Porosity, ft.$^3$/min./ft.$^2$ | 97 | 61 | 93 | 93.5 |
| Density, lbs./ft.$^3$ | 1.62 | 1.55 | 1.56 | 1.62 |
| ILD (4''), lbs./50 in.$^2$ | | | | |
| 25% deflection | 38.5 | 38.5 | 33.0 | 40.9 |
| 65% deflection | 70 | 65.8 | 58.4 | 76.1 |
| 25% return | 26.7 | 26.4 | 21.4 | 26.2 |
| Return value, % | 69.4 | 68.6 | 64.9 | 64.0 |
| Load Ratio | 1.82 | 1.71 | 1.77 | 1.86 |
| Compression Sets, % | | | | |
| 75% | 4.1 | 4.6 | — | — |
| 90% | — | — | 7.32 | 5.15 |
| Tensile strength, p.s.i. | 17.3 | 19.3 | 15.4 | 15.2 |
| Elongation, % | 204 | 232 | 215 | 173 |
| Tear Resistance, lbs./in. | 2.63 | 2.72 | 2.43 | 2.07 |
| Humid Age Load Loss, % /4/ | 6.8 | 8.17 | 9.18 | 14.7 |

/1/ Except for the variation in stannous octoate concentration and the amine catalyst employed, the composition of this formulation is as defined in Table VII.
/2/ 3-Dimethylamino-N,N-dimethylpropionamide.
/3/ 2-(N,N-dimethylamino)ethyl 3-dimethylaminopropionate.
/4/ Aged five hours at 120°C. in 100% relative humidity.

The results of Table VIII further indicate that the catalysts described herein are effective promoters of the water-isocyanate reaction and, as reflected by the relatively short rise time, Amine Catalyst I has particularly good reactivity in this respect. The data also indicate that the flexible foam products were highly porous and had a good overall combination of properties. For the purpose of comparison, it is noted that when 0.1 p.p.h.p. of a 70 weight percent solution of bis[2-N,N-dimethyl-amino)ethyl]ether (i.e., Amine Catalyst A) is employed as the sole amine catalyst of Foam Formulation D at the same stannous octoate level (0.30 p.p.h.p.) employed in Example 20, the resulting formulation provides a cream time of 10 seconds and a rise time of 80 seconds, and the flexible foam product has the following properties (expressed on the basis of the same units shown in Table VIII): porosity = 58.7; resiliency = 46; density = 1.45; 25% ILD = 39.1; load ratio = 1.72; 90% compression set = 3.36; tensile strength = 17.4; elongation = 235; and humid age load loss = 14.1.

EXAMPLES 24–30

A series of free-rise, flexible foams was prepared employing reaction mixtures containing the beta-amino carbonyl catalysts of the invention in combination with bis[2-(N,N-dimethylamino)ethyl]ether. The particular beta-amino carbonyl compounds employed were Amine Catalysts I-V, III and IX, respectively. The composition of the reaction mixtures, designated Foam Formulation E, is given in Table IX.

TABLE IX

FOAM FORMULATION E

| Component | Parts By Weight Control K-4 | Parts By Weight Examples 24-30 |
|---|---|---|
| Polyol E: A polyether triol having a Hydroxyl No. of 46 and containing less than 5 mole percent of primary hydroxyl groups, derived from glycerol, propylene oxide and ethylene oxide, about 14 weight per cent of total oxide being ethylene oxide. | 100 | 100 |
| Polyisocyanate B: An 80:20 mixture of the 2,4- and 2,6- isomers of tolylene diisocyanate, respectively. (Index = 105) | 48.2 | 48.2 |
| Water | 4.0 | 4.0 |
| Stannous octoate | 0.25 | 0.25 |
| Surfactant D /1/ | 1.0 | 1.0 |
| Amine Catalysts | | |
| Amine Catalyst A: A 70 weight per cent solution of bis[2-(N,N-dimethylamino)-ethyl]ether in dipropylene glycol. | 0.1 | — |
| Blend: A 67/33 parts by weight blend of Amine Catalysts I-V, VIII or IX and bis[2-(N,N-dimethylamino)ethyl]-ether. | — | 0.1 |

/1/ As defined in Table VII.

As indicated in Table IX, the catalysts employed in the examples were added as blends (0.1 part) containing 67 and 33 parts by weight of the beta-amino carbonyl compound and bis-ether, respectively, thereby providing 0.067 and 0.033 part by weight of each type of catalyst per 100 parts of polyol reactant (p.p.h.p.). As further indicated in Table IX, the control formulation employed in Control Run K-4, contained the bis-ether (0.070 p.p.h.p.) as the sole amine catalyst, added as 0.1 part of a 70 weight percent solution thereof. The various foams were prepared following Foam Procedure II. The results are given in Table X.

physical properties as compared with Control Foam K-4 and that certain individual properties were superior. Thus, in each instance, Foam Nos. 14–20 were markedly more porous than the control foam; particularly outstanding in this respect were Foam No. 14 based on Amine Catalyst I (3-dimethylamino-N,N-dimethylpropionamide), Foam No. 19 based on Amine Catalyst VIII [ethyl 3-(N,N-dimethylamino)propionate], and Foam No. 20 based on Amine Catalyst IX [ethyl 3-(N,N-diethylamino)propionate]. In addition to their enhanced porosity, Foam Nos. 14–20 also exhibited lower load loss values after humid aging than the control foam; expecially outstanding in this respect were Foam Nos. 15–18 based on Amine Catalysts II-V, respectively. Of further significance is the realization of these improvements without the necessity of employing catalysts associated with the odor characteristic of amines; freshly prepared Foams 146020 were odorless.

EXAMPLES 31–37

In accordance with these examples, another series of foams was prepared employing respective reaction mixtures based on the blends of Amine Catalysts I-V, VIII and IX described under Examples 24–30. The composition of the reaction mixtures (Foam Formulation F) including that employed in Control Run K-5 is given in Table XI.

TABLE XI

FOAM FORMULATION F

| Component | Parts By Weight Control K-5 | Parts By Weight Examples 31-37 |
|---|---|---|
| Polyol E /1/ | 100 | 100 |
| Polyisocyanate B /1/ (Index = 105) | 37.9 | 37.9 |
| Water | 3.0 | 3.0 |
| Stannous octoate | 0.275 | 0.275 |
| Surfactant E /2/ | 1.0 | 1.0 |
| Amine Catalysts | | |
| Amine Catalyst A: A 70 weight per cent solution of bis[2-(N,N-dimethylamino)ethyl]ether in dipropylene glycol. | 0.1 | — |
| Blend: A 67/33 parts by weight blend of Amine Catalysts I-V, VIII or IX and bis[2-(N,N-dimethylamino)ethyl]- | — | 0.1 |

TABLE X

| Example No. | — | 24 | 25 | 26 | 27 | 28 | 29 | 30 |
|---|---|---|---|---|---|---|---|---|
| Control Run No. | K-4 | — | — | — | — | — | — | — |
| Foam No. | K-4 | 14 | 15 | 16 | 17 | 18 | 19 | 20 |
| Foam Formulation E /1/ | | | | | | | | |
| Amine Catalyst No. | — | I | II | III | IV | V | VIII | IX |
| Parts By Weight p.h.p. | None | 0.067 | 0.067 | 0.067 | 0.067 | 0.067 | 0.067 | 0.067 |
| Bis[2-(N,N-dimethylamino)ethyl]ether, p.p.h.p. | 0.070 | 0.033 | 0.033 | 0.033 | 0.033 | 0.033 | 0.033 | 0.033 |
| Cream Time, seconds | 9 | 10 | 9 | 10 | 9 | 9 | 9 | 11 |
| Rise Time, seconds | 78 | 94 | 82 | 80 | 78 | 78 | 90 | 90 |
| Foam Properties | | | | | | | | |
| Resiliency, % ball rebound | 45 | 44 | 42 | 44 | 47 | 43 | 42 | 42 |
| Porosity, ft.$^3$/min./ft.$^2$ | 55.5 | 107.5 | 73.6 | 75.8 | 73.6 | 75.8 | 90.4 | 97.4 |
| Density, lbs./ft.$^3$ | 1.53 | 1.60 | 1.61 | 1.56 | 1.59 | 1.62 | 1.63 | 1.66 |
| ILD (4''), lbs./50 in.$^2$ | | | | | | | | |
| 25% deflection | 39.1 | 38.6 | 37.8 | 38.4 | 36.2 | 36.0 | 42.8 | 41.7 |
| 65% deflection | 66.0 | 66.8 | 69.9 | 69.5 | 66.9 | 67.4 | 73.2 | 73.4 |
| 25% return | 24.7 | 24.6 | 24.5 | 24.1 | 24.0 | 23.9 | 26.3 | 25.8 |
| Return value, % | 63.2 | 63.7 | 64.8 | 63.5 | 66.3 | 66.4 | 61.4 | 61.9 |
| Load Ratio | 1.69 | 1.73 | 1.85 | 1.81 | 1.84 | 1.87 | 1.71 | 1.76 |
| Compression Sets, % | | | | | | | | |
| 90% | 5.50 | 5.51 | 7.33 | 7.14 | 8.13 | 6.95 | 4.66 | 5.12 |
| 50% After Humid Aging /2/ | 6.23 | 6.56 | 11.1 | 10.6 | 11.8 | 11.3 | 6.02 | 5.94 |
| Tensile strength, p.s.i. | 20.0 | 17.4 | 18.3 | 18.5 | 19.4 | 19.1 | 17.20 | 17.1 |
| Elongation, % | 273 | 248 | 279 | 292 | 290 | 284 | 233 | 245 |
| Tear Resistance, lbs./in. | 3.14 | 3.02 | 4.20 | 3.58 | 3.61 | 3.60 | 3.47 | 3.02 |
| Humid Aged Load Loss, % /2/ | 24.8 | 20.2 | 16.6 | 14.8 | 14.5 | 15.8 | 18.7 | 18.5 |

/1/ As defined in Table IX.
/2/ After aging for five hours at 120°C. in 100% relative humidity.

The results of Table X indicate that the blended amine catalysts employed in Examples 24–30 provided flexible foams having an overall good combination of of Amine Catalysts I-V, VIII or IX
and bis[2-(N,N-dimethylamino)ethyl]-

TABLE XI-continued

FOAM FORMULATION F

| Component | Parts By Weight Control K-5 | Parts By Weight Examples 31–37 |
|---|---|---|
| ether. | | |

/1/ As defined in Table IX.
/2/ A polysiloxane-polyoxyalkylene block copolymer having the average composition $Me_3SiO(Me_2SiO)_{72}[MeO(C_3H_6O)_{28}(C_2H_4O)_{20}C_3H_6SiMeO]_{5.1}SiMe_3$, where Me is methyl, employed as a 55 weight per cent active solution.

The foams of these examples as well as the control foam were prepared following Foam procedure II. The results are given in Table XII.

TABLE XII

| Example No. | — | 31 | 32 | 33 | 34 | 35 | 36 | 37 |
|---|---|---|---|---|---|---|---|---|
| Control Run No. | K-5 | — | — | — | — | — | — | — |
| Foam No. | K-5 | 21 | 22 | 23 | 24 | 25 | 26 | 27 |
| Foam Formulation F /1/ | | | | | | | | |
| Amine Catalyst No. | — | I | II | III | IV | V | VIII | IX |
| Parts By Weight p.h.p. | None | 0.067 | 0.067 | 0.067 | 0.067 | 0.067 | 0.067 | 0.067 |
| Bis[2-(N,N-dimethylamino)ethyl]ether, p.p.h.p. | 0.070 | 0.033 | 0.033 | 0.033 | 0.033 | 0.033 | 0.033 | 0.033 |
| Cream Time, seconds | 7 | 11 | 11 | 11 | 10 | 10 | 10 | 12 |
| Rise Time, seconds | 95 | 118 | 106 | 106 | 100 | 101 | 120 | 128 |
| Foam Properties | | | | | | | | |
| Resiliency, % ball rebound | 46 | 49 | 44 | 43 | 45 | 46 | 29 | 29 |
| Porosity, ft.$^3$/min./ft.$^2$ | 18.1 | 41.7 | 14.2 | 9.7 | 29.2 | 30.8 | 4.2 | 1.7 |
| Density, lbs./ft.$^3$ | 1.83 | 1.98 | 1.91 | 1.88 | 1.91 | 1.90 | 1.85 | 1.88 |
| ILD (4"), lbs./50 in.$^2$ | | | | | | | | |
| 25% deflection | 34.6 | 40.0 | 37.0 | 35.6 | 34.6 | 34.0 | 45.0 | 45.4 |
| 65% deflection | 62.0 | 71.4 | 66.8 | 66.4 | 63.5 | 62.4 | 77.4 | 78.0 |
| 25% return | 24.0 | 27.8 | 25.1 | 24.4 | 24.0 | 23.6 | 30.3 | 30.5 |
| Return value, % | 69.4 | 69.4 | 67.8 | 68.5 | 69.4 | 69.4 | 67.3 | 67.2 |
| Load Ratio | 1.79 | 1.79 | 1.81 | 1.87 | 1.85 | 1.84 | 1.72 | 1.72 |
| Compression Sets, % | | | | | | | | |
| 90% | 6.62 | 4.73 | 6.73 | 6.28 | 5.67 | 5.44 | 6.00 | 5.07 |
| 50% After Humid Aging /2/ | 6.92 | 4.95 | 8.87 | 8.70 | 8.11 | 7.64 | 5.52 | 5.86 |
| Tensile strength, p.s.i. | 17.2 | 15.6 | 19.5 | 18.8 | 18.1 | 19.6 | 15.90 | 16.4 |
| Elongation, % | 291 | 217 | 301 | 294 | 300 | 333 | 210 | 223 |
| Tear Resistance, lbs./in. | 3.45 | 2.98 | 3.20 | 2.90 | 3.00 | 3.22 | 1.99 | 2.27 |
| Humid Aged Load Loss, % /2/ | 26.8 | 24.6 | 16.73 | 20.7 | 19.1 | 20.0 | 22.4 | 24.9 |

/1/ As defined in Table XI.
/2/ After aging for five hours at 120°C. in 100% relative humidity.

As indicated by data of Table XII and as recognized in its use, Foam Formulation F is a difficult reaction mixture to prepare as a commercially open, porous product. Thus it was not surprising that Control Foam K-5, as well as Foam Nos. 22, 23, 26 and 27, had porosity values less than 20. On the other hand, it was unexpected to find that under this unfavorable condition, Foam Nos. 21, 24 and 25 based on Amine Catalysts I, IIV and V, had acceptable open, porous structures as reflected by their respective porosity values of 41.7, 29.2 and 30.8.

EXAMPLES 38–46

The purpose of these examples is to illustrate the efficacy of the beta-amino carbonyl compounds as catalytic components of flame-retarded foam formulations (Examples 38–43) and their operating latitude with respect to variation in concentration of tin cocatalyst in such formulations as well as in non flameretarded systems (Examples 44–46). The compositions of the reaction mixtures are given in Table XIII. In Examples 38–45, the amine catalysts were added to the formulation as an 80:20 parts by weight blend of Amine Catalyst I and bis[2-(N,N-dimethylamino)ethyl]ether, respectively. A 67/33 parts by weight blend of these catalysts was used in Example 46. Based on 100 parts of polyol inclusive of flame-retardant when present, either 0.1 or 0.2 part of the respective blends were used. The foams were formed following Foam Procedure II. The results are given in Table XIII wherein "SE" indicates that the foam sample qualified for a self-extinguishing rating under flammability test ASTM D-1692-67T. Table XIII also includes data, as Runs A and B, by way of illustrating a common effect that flame-retardants often have on flexible foam porosity.

TABLE XIII

| Example No. | — | — | 38 | 39 | 40 | 41 | 42 | 43 | 44 | 45 | 46 |
|---|---|---|---|---|---|---|---|---|---|---|---|
| Run No. | A | B | — | — | — | — | — | — | — | — | — |
| Foam No. | A | B | 28 | 29 | 30 | 31 | 32 | 33 | 34 | 35 | 36 |
| Formulation, Parts By Weight | | | | | | | | | | | |
| Polyol D /1/ | 90 | 90 | 90 | 90 | 90 | 90 | 90 | 90 | 100 | 100 | 100 |
| Dibromoneopentyl glycol | 10 | 10 | 10 | 10 | 5 | 5 | 5 | — | — | — | |
| Tribromoneopentyl alcohol | — | — | — | — | 10 | 5 | 5 | 5 | — | — | — |
| Polyisocyanate B /1/ (Index = 105) | 55.8 | 55.8 | 55.8 | 55.8 | 51.63 | 53.72 | 53.72 | 53.72 | 49.7 | 49.7 | 49.7 |
| Water | 4.0 | 4.0 | 4.0 | 4.0 | 4.0 | 4.0 | 4.0 | 4.0 | 4.0 | 4.0 | 4.0 |
| Stannous octoate | 0.10 | 0.10 | 0.10 | 0.10 | 0.275 | 0.175 | 0.20 | 0.20 | 0.325 | 0.40 | 0.35 |
| Surfactant D /1/ | 1.0 | 1.0 | — | — | — | — | — | — | — | — | 1.0 |
| Surfactant F /2/ | — | — | 0.45 | 0.45 | 0.45 | 0.45 | 0.45 | 0.45 | 0.45 | 0.45 | — |
| Bis[2-(N,N-dimethylamino)ethyl]ether | 0.07 | 0.03 | 0.02 | 0.04 | 0.04 | 0.04 | 0.04 | 0.02 | 0.02 | 0.04 | 0.033 |
| Amine Catalyst I | — | — | 0.08 | 0.16 | 0.16 | 0.16 | 0.16 | 0.08 | 0.08 | 0.16 | 0.067 |
| Cream Time, seconds | 7 | 7 | 13 | 11 | 11 | 12 | 11 | 13 | 11 | 9 | 12 |
| Rise Time, seconds | 89 | 101 | 135 | 112 | 81 | 92 | 87 | 101 | 85 | 68 | 95 |
| Foam Properties | | | | | | | | | | | |
| Resiliency, % ball rebound | Closed foam | closed foam | 36 | 37 | 38 | 37 | 33 | 34 | 45 | 45 | 44 |
| Porosity, ft.$^3$/min./ft.$^2$ | " | " | 73 | 60 | 90 | 80.6 | 61.3 | 42.3 | 68.7 | 61.6 | 80.7 |
| Density lbs./ft.$^3$ | " | " | 1.47 | 1.47 | 1.43 | 1.43 | 1.40 | 1.42 | 1.46 | 1.45 | 1.58 |
| ILD (4"), lbs. 50/in.$^2$ | | | | | | | | | | | |
| 25% deflection | " | " | 34.2 | 29.6 | 32.1 | 34.1 | 36.0 | 38.1 | 33.4 | 35.0 | 40.2 |

TABLE XIII-continued

| | | | | | | | | | | |
|---|---|---|---|---|---|---|---|---|---|---|
| 65% deflection | " | " | 63.6 | 56.4 | 55.2 | 59.8 | 65.1 | 68.5 | 61.0 | 61.8 | 74.0 |
| 25% return | " | " | 19.8 | 17.4 | 17.8 | 19.3 | 20.4 | 20.9 | 21.0 | 22.1 | 25.2 |
| Return value, % | " | " | 57.8 | 58.7 | 55.4 | 56.6 | 56.7 | 54.8 | 62.8 | 63.2 | 62.7 |
| Load Ratio | " | " | 1.86 | 1.91 | 1.72 | 1.75 | 1.81 | 1.80 | 1.83 | 1.77 | 1.84 |
| 90% Compression Set, % | " | " | 23.6 | 36.3 | 13.9 | 90.6 | 21.4 | 25.8 | 7.12 | 6.97 | 5.69 |
| 50% Compression Set, % /3/ | " | " | 65.2 | 67.3 | 12.5 | 27.4 | 41.5 | 53.6 | 9.20 | 9.12 | 5.68 |
| Tensile strength, p.s.i. | " | " | 18.7 | 19.6 | 15.8 | 18.9 | 16.9 | 18.2 | 16.5 | 17.0 | 16.0 |
| Elongation, % | " | " | 195 | 215 | 231 | 236 | 232 | 240 | 240 | 237 | 215 |
| Tear Resistance, lbs./in. | " | " | 3.06 | 2.98 | 2.71 | 2.90 | 2.96 | 2.96 | 2.58 | 2.72 | 2.33 |
| Humid Age Load Loss, % /3/ | " | " | 12.9 | 6.85 | 7.24 | 11.9 | 6.68 | 5.70 | 9.22 | 6.69 | 16.5 |
| Flammability (ASTM D-1692-67) | | | | | | | | | | | |
| Extinguishing time, seconds | " | " | 17 | 17 | 31.4 | 23.1 | | | | | |
| Burning extent, inches | " | " | 1.50 | 1.56 | 2.41 | 1.88 | | | | | |
| Burning rate, in./min. | " | " | 5.1 | 5.33 | 4.62 | 4.89 | | | | | |
| Flame-rating | " | " | SE | SE | SE | SE | | | | | |

/1/ As defined in Table VII.
/2/ A polysiloxane-polyoxyalkylene block copolymer having the average composition, $Me_3SiO(Me_2SiO)_{60}[NC(CH_2)_3SiMeO]_{10}[MeO(C_3H_6O)_{30}(C_2H_4O)_{28.4}C_3H_6SiMeO]_6$. $SiMe_3$, where Me is methyl.
/3/ After aging for 5 hours at 120°F. in 100% relative humidity.

The results of Examples 38–43 indicate that the present discovery of amine urethane catalysts which are capable of providing very high porosity polyurethane foam is of particular value in the preparation of highly porous, flame-retarded foams. The more usual result is illustrated by Run Nos. A and B wherein the inclusion of the reactive flame-retardant, dibromoneopentyl glycol, provided foams that shrank completely. It should be understood that the excellent flammability properties of the foams produced in Examples 38–43 is in large measure attributable to the particular cyanopropylmodified silicone surfactant (Surfactant F) employed. Thus, when the beta-amino carbonyl catalysts of this invention are employed in combination with this surfactant, particularly effective formulations are provided for preparing open, highly porous flexible foams having excellent flame-retardant character. The data of Table XIII also show that these desirable results are realized under a variety of conditions and that increasing the tin co-catalyst (stannous octoate) levels to upgrade foam physical properties can be accomodated and still retain foam processability.

The versatility of the beta-amino carbonyl compounds as effective catalytic components of a wide variety of reaction mixtures is further demonstrated by the following Examples 47 and 48 drawn to the preparation of rigid polyurethane foams. In preparing these foams, all components except the polyisocyanate reactent were mixed for 15 seconds and, after appropriate adjustment for loss of fluorocarbon blowing agent, mixing was continued for an additional 15 seconds. The organic polyisocyanate was then added and, after mixing the complete formulation for 5 seconds, it was poured into an open box (12 inches × 12 inches × 12 inches). Rise was measured until the rate of the rise was less than one millimeter per 10 seconds.

EXAMPLE 47

The rigid foam formulation employed in this example contained (on a weight basis): (a) 100 parts of a sucrose-based polyol having a hydroxyl number of about 400 prepared as a mixed adduct of sucrose, diethylenetriamine and aniline; (b) 108 parts of a tolylene diisocyanate produced as a residue product in the manufacture of the 2,4- and 2,6- isomers of tolylene diisocyanate and having a free —NCO content of about 38.5 weight percent (Index - 108); (c) 1.6 parts of water; (d) 44 parts of inhibited trichlorofluoromethane blowing agent; (e) 1.5 parts of a tin catalyst; and (f) 2 parts of 3-dimethylamino-N,N-dimethylpropionamide (Amine Catalyst I). For the purpose of comparison, a control formulation was employed containing the aforesaid components (a)–(e) and, as amine catalyst component (f), 2 parts of dimethylethanolamine in place of Amine Catalyst I. Formulation reactivity is indicated by the following results, the values within parenthesis applying to the control formulation: Cream time = 10 (8) seconds; Gel time = 25 (35) seconds; Tack-free time = 35 (50) seconds; and Rise time = 35 (55) seconds. The lower gel, tack-free and rise times indicate that the formulation containing Amine Catalyst I was the more reactive formulation. In both instances rigid foams of satisfactory quality were obtained.

EXAMPLE 48

In accordance with this example, a rigid foam was prepared employing the following components (on a weight basis): (a) 85 parts of a sorbitol-based polyol having a Hydroxyl No. of about 490 and a molecular weight of about 700, derived from sorbitol, dipropylene glycol and propylene oxide; (b) 13 parts of an amine pentol having a Hydroxyl No. of about 700, derived from diethylenetriamine and propylene oxide; (c) 2 parts of glycerol; (d) 148 parts of a polyphenylmethylene polyisocyanate having an average —NCO functionality of 2.7 and a free —NCO content of 30.5–32.3 weight percent (Index = 115); (e) 41 parts of trichlorofluoromethane blowing agent; (f) 4.2 parts of flame-retardant [0,0-diethyl-N,N-bis(2-hydroxyethyl)aminomethyl phosphonate]; (g) 1.6 parts of surfactant (Union Carbide Corporation Silicone Surfactant L-5420); (h) 0.4 part of N,N,N',N'-tetramethylbutanediamine; and (i) 1.2 parts of 3-dimethyl-amino-N,N-dimethylpropionamide (Amine Catalyst I). For the purpose of comparison, a control foam was prepared employing the above formulation except that in place of Amine Catalyst I, 1.2 parts of Amine Catalyst B was used (that is, a 33 weight percent solution of triethylene-diamine in dipropylene glycol). Formulation reactivity was as follows wherein corresponding data for the control are given in parenthesis: Cream time = 60 (35) seconds; Gel time = 100 (85) seconds; Tack-free time = 190 (110) seconds; Rise time = 200 (130) seconds. These data show that, although reactivity of the control formulation was higher, Amine Catalyst I provided satisfactory results in this respect. In both instances, rigid foams of satisfactory quality were obtained.

What is claimed is:

1. As novel compositions, 3-(N-morpholino)-N',N'-dialkylamides having the formula,

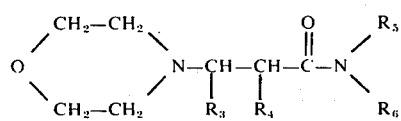

wherein: $R_3$ and $R_4$ are hydrogen or alkyl of one to four carbon atoms; and $R_5$ and $R_6$ are alkyl of one to four carbon atoms.

2. 3-(N-morpholino)-N',N'-dialkylamides as defined in claim 1 in which $R_5$ and $R_6$ are methyl or ethyl, and at least one of $R_3$ and $R_4$ is hydrogen and the other is hydrogen, methyl or ethyl.

3. 3-(N-morpholino)-N',N'-dimethylpropionamide.

* * * * *

UNITED STATES PATENT OFFICE
CERTIFICATE OF CORRECTION

Page 1 of 2

Patent No. 3,954,749    Dated May 4, 1976

Inventor(s) David C. Priest, Michael R. Sandner, David J. Trecker

It is certified that error appears in the above-identified patent and that said Letters Patent are hereby corrected as shown below:

Column 1, line 9, for "betamino" read -- beta-amino --; line 14, for "polyisocynates" read -- polyisocyanates --; line 44, for "poluurethane" read -- polyurethane --. Column 2, line 19, for "morphine" read -- morpholine --. Column 3, line 52, for "repsect" read -- respect --. Column 5, line 17, for "N,N'-piperazonobis" read -- N,N'-piperazino-bis --; Formula III-A, that portion reading Column 5, line 36, for "ad" read -- and --. Column 6, line 15, for "-diamethylamino)" read -- -dimethylamino) --. Column 9, line 25, for "stiochiometry" read -- stoichiometry --.
Column 10, line 3, for "amine" read -- amino --. Column 11, line 31, for "beta-amine" read -- beta-amino --. Column 19, line 53, for "1.6" read -- 0.6 --. Column 21, line 51, for "forumla" read -- formula --. Column 23, line 68, after "process" read -- is --. Column 25, line 39, for "Amine" read -- amine --. Column 26, Table I, in each occurrence, that portion of each of the second and fourth formulas reading

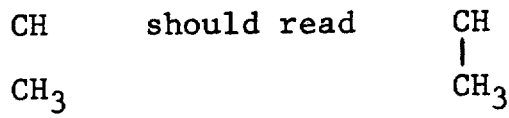

Column 28, line 55, for "weighted" read -- weighed --.
Column 29, line 6, for "weighted" read -- weighed --.
Column 30, line 1, for "flanges" read -- flanged --; line 41, for "Amino" read -- Amine --; line 43, for "catalyst" read -- catalytic --. Column 31, line 18, for "Exampes" read -- Examples --; line 30, for "demoled" read -- demold --;

UNITED STATES PATENT OFFICE
CERTIFICATE OF CORRECTION

Patent No. 3,954,749     Dated May 4, 1976

Inventor(s) David C. Priest, Michael R. Sandner, David J. Trecker

It is certified that error appears in the above-identified patent and that said Letters Patent are hereby corrected as shown below:

line 37, for "in" read -- an --. Column 33, line 36, for "is" read -- in --. Column 35, line 67, for "indicated" read -- indicate --. Column 36, line 2, for "valves" read -- values --; line 3, for "completly" read -- completely --. Column 37, line 3, for "III" read -- VIII --. Column 38, line 13, for "expecially" read -- especially --; line 18, for "146020" read -- 14-20 --. Column 39, line 48, for "IIV" read -- IV --. Column 41, lines 46-47, for "reactent" read -- reactant --.

Signed and Sealed this

Twenty-first Day of June 1977

[SEAL]

Attest:

RUTH C. MASON
Attesting Officer

C. MARSHALL DANN
Commissioner of Patents and Trademarks